(12) United States Patent
Cervin et al.

(10) Patent No.: US 8,512,982 B2
(45) Date of Patent: Aug. 20, 2013

(54) ENHANCED PROTEIN PRODUCTION IN BACILLUS

(75) Inventors: Marguerite A. Cervin, Redwood City, CA (US); Eugenio Ferrari, San Bruno, CA (US); Scott D. Power, San Bruno, CA (US)

(73) Assignee: Danisco US Inc., Palo Alto, CA (US)

( * ) Notice: Subject to any disclaimer, the term of this patent is extended or adjusted under 35 U.S.C. 154(b) by 167 days.

(21) Appl. No.: 12/743,187

(22) PCT Filed: Dec. 19, 2008

(86) PCT No.: PCT/US2008/087633
§ 371 (c)(1),
(2), (4) Date: Jan. 13, 2011

(87) PCT Pub. No.: WO2009/094084
PCT Pub. Date: Jul. 30, 2009

(65) Prior Publication Data
US 2011/0117598 A1     May 19, 2011

(51) Int. Cl.
*C12P 21/02*     (2006.01)
*C12N 15/63*     (2006.01)
*C07H 21/04*     (2006.01)

(52) U.S. Cl.
USPC ............... 435/69.1; 435/252.31; 435/320.1; 435/471; 536/23.7

(58) Field of Classification Search
None
See application file for complete search history.

(56) References Cited

PUBLICATIONS

Feng-Xia Qi et al Localization of a Second SigH Promoter in the *Bacillus subtilis* sigA Operon and Regulation of dnaE Expression by the Promoter Journal of Bacteriology, Oct. 1990, p. 5631-5636.*
Arigoni et al. "The SpoIIE phosphatase, the sporulation septum and the establishment of forespore-specific transcription in *Bacillus subtilis*: a reassessment." *Mol. Microbiol.*31:1407-1415, 1999.
Britton et al. "Genome-Wide Analysis of the Stationary-Phase Sigma Factor (Sigma-H) Regulon of *Bacillus subtilis.*" *J. Bacteriol.* 184(7):4881-4890, Sep. 2002.
Caldwell et al. "Correlation between *Bacillus subtilis* scoC Phenotype and Gene Expression Determined Using Microarrays for Transcriptome Analysis." *J. Bacteriol.*183(24):7329-7340, 2001.
Database SwissProt Accession No. O31796, updated Jan. 1, 1998, 3 pp.
Henner et al. "The *Bacillus subtilis* Chromosome." *Microbiol. Rev.* 44(1): 57-82, Mar. 1980.
International Search Report for PCT/US2008/087633 mailed Jun. 24, 2009, 2 pp.
Kunst et al. "The complete genome sequence of the Gram-positive bacterium *Bacillus subtilis.*" *Nature* 390: 249-256, 1997.
Moszer, I. "The complete genome of *Bacillus subtilis*: from sequence annotation to data management and analysis." *FEBS Lett*.430: 28-36, 1998.
Msadek et al. "Signal Transduction Pathway Controlling Synthesis of a Class of Degradative Enzymes in *Bacillus subtilis*: Expression of the Regulatory Genes and Analysis of Mutations in *degS* and *degU.*" *J. Bacteriol.* 172(2): 824-834, Feb. 1990.
Sauter et al. "Sm-like proteins in Eubacteria: the crystal structure of the Hfq protein from *Escherichia coli.*" *Nucleic Acids Res.* 31(14): 4091-4098, 2003.
Silvaggi et al., "Small Untranslated RNA Antitoxin in *Bacillus subtilis.*" *J Bacteriol*.187(19): 6641-6650, 2005.
Stahl et al. "Replacement of the *Bacillus subtilis* Subtilisin Structural Gene with an In Vitro-Derived Deletion Mutation." *J. Bacteriol.* 158(2): 411-418, May 1984.
Storz et al. "Controlling mRNA Stability and Translation with Small, Noncoding RNAs," *Current Opinion in Microbiology* 7(2):140-144, Apr. 2004.
Widner et al. "Development of Marker-Free Strains of *Bacillus subtilis*capable of secreting high levels of industrial enzymes," *J. Industrial Microbiol. & Biotech.* 25(4):204-212, Oct. 2000.

* cited by examiner

*Primary Examiner* — Kagnew H Gebreyesus
(74) *Attorney, Agent, or Firm* — Danisco US Inc.

(57) ABSTRACT

The present invention relates to cells that have been genetically manipulated to have an altered capacity to express and/or produce proteins of interest. In particular, the present invention relates to modified host cells of Gram-positive microorganisms, such as *Bacillus* species that are capable of overexpressing ymaH. The invention encompasses polynucleotide constructs and expression vectors containing polynucleotide sequences that encode YmaH, and the modified host cells comprising them. In particular, the present invention relates to compositions and methods of overexpressing YmaH for enhancing the expression and production of proteins of interest (e.g., proteases) in *Bacillus* species.

28 Claims, 5 Drawing Sheets

TCATACCCTGAAAGGAAAGACAAGGAAATTGTCGGCAATGAGCCGCTCGGCAGGTAGAAGGATGTTTACCGATGCAAAAAAA

GGGCAAAATGATAGGTGGTTGTCCATGTTGAATGCTATAATGGGGGAGATTTATAAAGAGAGTGATACATATTGAATAATAC
miaA coding →
GAAGCAGCCCGTTGTCATTTTAGTCGGACCGACGGCAGTGGGGAAAACCAATTTAAGTATTCAGCTAGCCAAATCCTTAAACGC GGAAATTATCAGCGGAGATTCGATGCAGATTTATAAAGGGATGGATATTGGAACAGCTAAAATTACCGAACAGGAGATGGAGGG AGTGCCCCATCATCTGATTGACATTTTAGATCCCCAAGACTCTTTCTCTACTGCCGATTATCAAAGCTTAGTAAGAAATAAAATCA GCGAGATTGCAAATAGAGGAAAGCTTCCGATGATTGACGGCCGGTACAGGGCTTTATATACAATCTGAGCTTTACGATTATACATT TACGGAAGAGGCAAATGATCCCGTGTTTCGAGAGAGCATGCAAATGGCTGCTGAGCGGGAAGGCGCTGACTTCTTCATGCCA AACTTGCTGCAGCAGATCCCGAGGCAGCAGCTGCGATTCATCCGAATAATACAAGAGAACTTCTGTACAATGCAGTGTTAATTGGCCTGACAAT ATACGTCCGAAAACGATGTCCCAGCATTTGAAGGAACAAAAAACGAGAACTTCTGTACAATGCAGTGTTAATTGGCCTGACAAT GGATAGAGACACGCTTTACGAAAGAATTAATCAGCGGGTCGATTTGATGATGCAGTCAGGCCTTCTTCCGAAGTGAAACGCTT ATACGACAAGAACGTGAGAGACTGTCAATCAATACAGGCGATAGGCTATAAAGAGCTGTATGCATATTTGACGGTTTGTGACA

CTTTCCGATGCTGTCGAACAGCTAAAGCAACTCGAGGCGGTATGCGAAACGCCAGCTGGTTTCGCAACAAAATGCA

GGTCACATGGTTCGATATGACACCGCCTGTTGATATGGAGCTGAAAAAAAGGAAATTTCACACATATAGCAGGAAAACTCGA

ACTTTAATCGAAACTGTATGATATAGAGAATCAAGGAGGACGAAACATGAAACGATTAATATTCAGGATCAGTTTTGAATCA
ymaH coding →
AATCCGGAAAGAAAATACGTATGTCACTGTTTTTTGCTGAAGCAGCAGCTTATATATAAACATGCGATCTCAACGTTTGCGCCGCAAAAACGT

TTACCGTATTGTTGGAATCGGAAGTAAGCAGCAGCTTATATATAAACATGCGATCTCAACGTTTGCGCCGCAAAAACGT

CCAGCTTGAACTCGAATAGATCAAAAATGCCATGTCAAGACATGAGGAAAGGCTGTGGGGGTTCCGGCGGCCATTTTAA

CATGAATCCACTTTTGCTCCAAGCTTTTGTGTAAGCTGACCATGCCAAGGCACGCGGTCTTTTTTATGAG

Figure 2

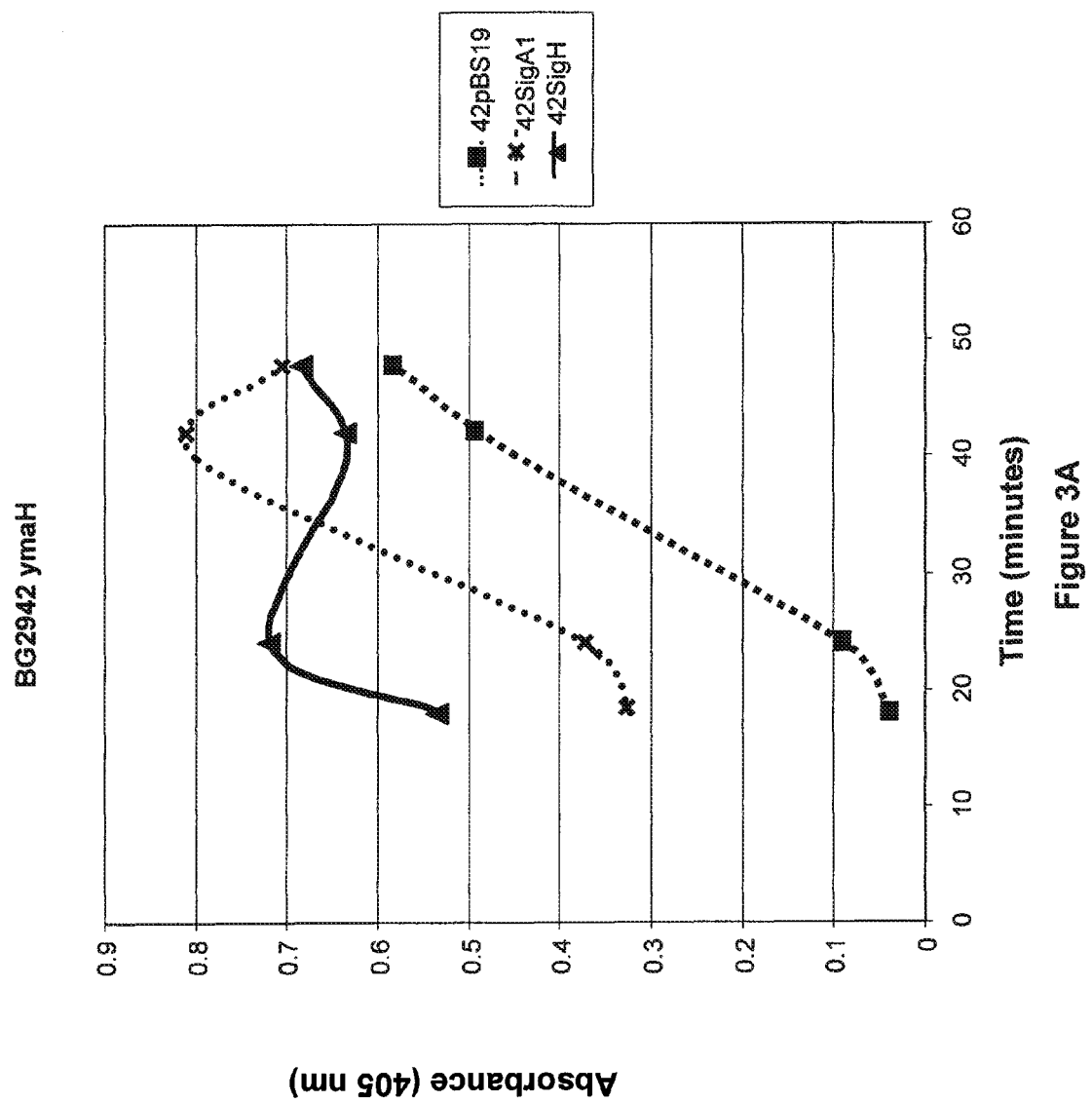

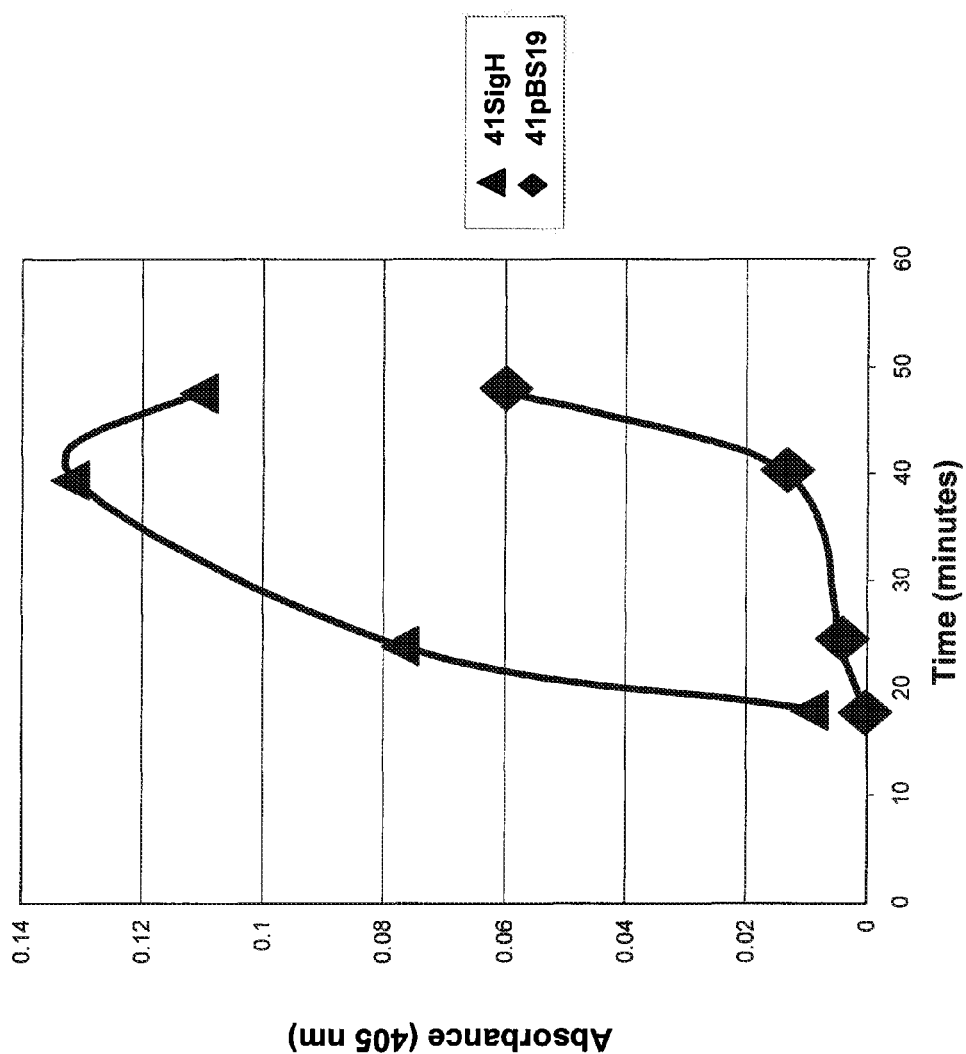

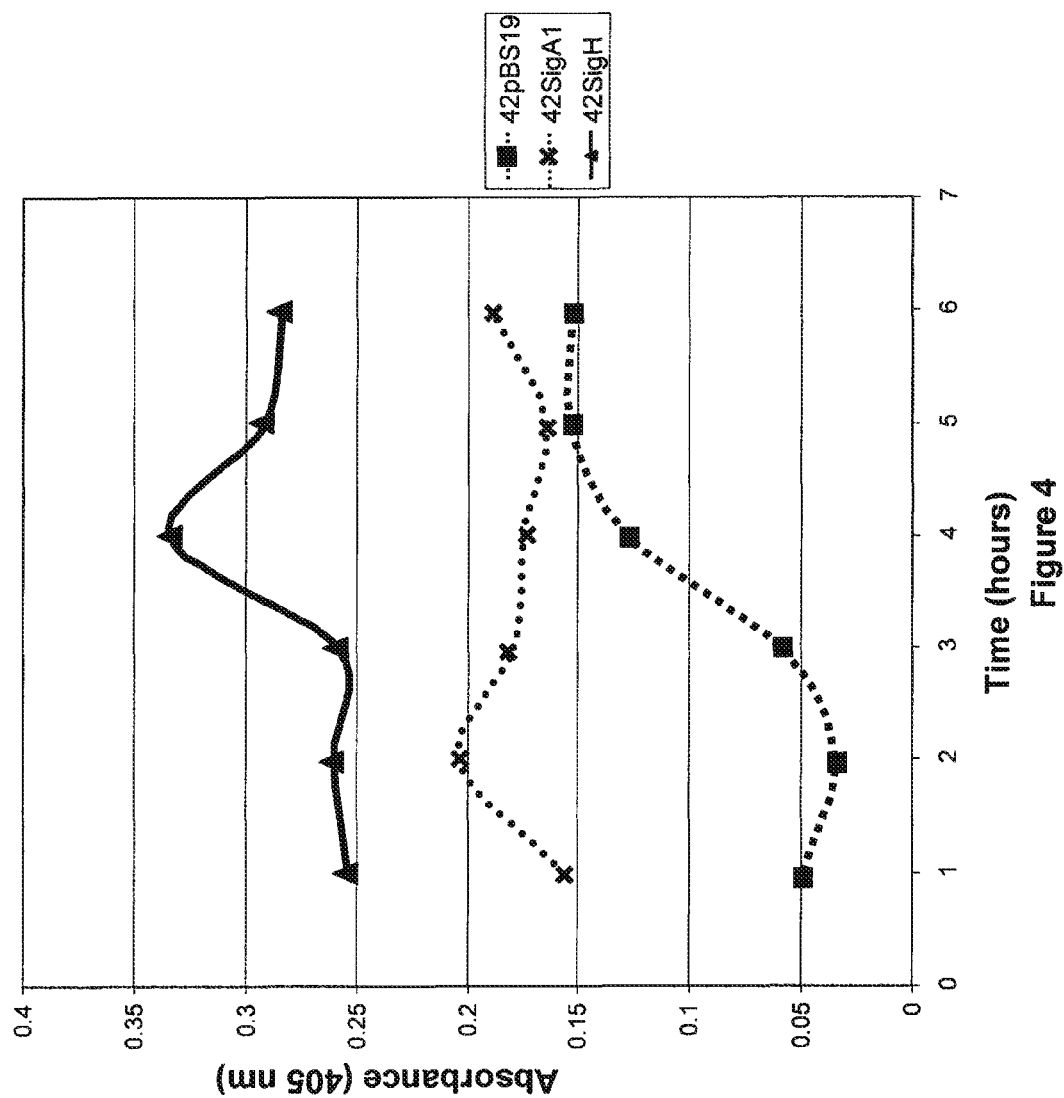

US 8,512,982 B2

ENHANCED PROTEIN PRODUCTION IN *BACILLUS*

CROSS-REFERENCE TO RELATED APPLICATIONS

This application is a National Stage Application under 35 U.S.C. §371 of International Application No. PCT/US2008/087633, filed Dec. 19, 2008, which claims the benefit of U.S. Provisional No. 61/016,376, filed Dec. 21, 2007.

FIELD OF THE INVENTION

The present invention relates to cells that have been genetically manipulated to have an altered capacity to express and/or produce proteins of interest. In particular, the present invention relates to modified host cells of Gram-positive microorganisms, such as *Bacillus* species that are capable of overexpressing ymaH. The invention encompasses polynucleotide constructs and expression vectors containing polynucleotide sequences that encode YmaH, and the modified host cells comprising them. In particular, the present invention relates to compositions and methods of overexpressing ymaH for enhancing the expression and production of proteins of interest (e.g., proteases) in *Bacillus* species.

BACKGROUND OF THE INVENTION

Genetic engineering has allowed the improvement of microorganisms used as industrial bioreactors, cell factories and in food fermentations. In particular, *Bacillus* species produce and secrete a large number of useful proteins and metabolites (Zukowski, "Production of commercially valuable products," In: Doi and McGlouglin (eds.) *Biology of Bacilli: Applications to Industry*, Butterworth-Heinemann, Stoneham. Mass pp 311-337 [1992]). The most common *Bacillus* species used in industry are *B. licheniformis, B. amyloliquefaciens* and *B. subtilis*. Because of their GRAS (generally recognized as safe) status, strains of these *Bacillus* species are natural candidates for the production of proteins utilized in the food and pharmaceutical industries. Important production enzymes include α-amylases, neutral proteases, and alkaline (or serine) proteases. However, in spite of advances in the understanding of production of proteins in *Bacillus* host cells, there remains a need for methods to improve the expression and production of these proteins by microorganisms.

SUMMARY OF THE INVENTION

The present invention relates to cells that have been genetically manipulated to have an altered capacity to express and/or produce proteins of interest. In particular, the present invention relates to modified host cells of Gram-positive microorganisms, such as *Bacillus* species that are capable of overexpressing ymaH. The invention encompasses polynucleotide constructs and expression vectors containing polynucleotide sequences that encode YmaH, and the modified host cells comprising them. In particular, the present invention relates to compositions and methods of overexpressing ymaH for enhancing the expression and production of proteins of interest (e.g., proteases) in *Bacillus* species.

In one embodiment, the invention provides an isolated chimeric polynucleotide that comprises a polynucleotide sequence defining a SigA promoter operably linked a polynucleotide encoding a YmaH protein.

In another embodiment, the invention provides an isolated chimeric polynucleotide that comprises a polynucleotide sequence defining a SigA promoter operably linked to a polynucleotide encoding a YmaH protein, wherein the chimeric polynucleotide comprises SEQ ID NO:2 or SEQ ID NO:3.

In another embodiment, the invention provides a vector comprising a polynucleotide construct that comprises a polynucleotide encoding a YmaH protein operably linked to a sigA and/or a sigH promoter polynucleotide sequence.

In another embodiment, the invention provides a vector comprising a polynucleotide construct that comprises a polynucleotide encoding a YmaH protein operably linked to a sigA and/or a sigH promoter polynucleotide sequence, wherein the polynucleotide construct comprises SEQ ID NO:1, 2, 3 or 13.

In another embodiment, the invention provides a modified *Bacillus* cell that comprises a vector comprising a polynucleotide construct that comprises a polynucleotide encoding a YmaH protein operably linked to a sigA and/or a sigH promoter polynucleotide sequence, wherein the modified cell is capable of producing a protein of interest.

In another embodiment, the invention provides a modified *Bacillus* host cell that is chosen from the group consisting of *B. licheniformis, B. subtilis, B. lentus, B. brevis, B. stearothermophilus, B. alkalophilus, B. amyloliquefaciens, B. coagulans, B. circulans, B. lautus, B. pumilus, B. thuringiensis, B. clausii*, and *B. megaterium* and comprises a vector comprising a polynucleotide construct that comprises a polynucleotide encoding a YmaH protein operably linked to a sigA and/or a sigH promoter polynucleotide sequence, wherein the modified cell is capable of producing a protein of interest.

In another embodiment, the invention provides a modified *Bacillus* host cell that comprises a vector comprising a polynucleotide construct that comprises a polynucleotide encoding a YmaH protein operably linked to a sigA and/or a sigH promoter polynucleotide sequence, wherein the modified cell is capable of producing a protein of interest that is homologous or heterologous to the modified cell.

In another embodiment, the invention provides a modified *Bacillus* host cell that comprises a vector comprising a polynucleotide construct that comprises a polynucleotide encoding a YmaH protein operably linked to a sigA and/or a sigH promoter polynucleotide sequence, wherein the modified cell is capable of producing a protein of interest, and wherein an aprE promoter drives the expression of said protein of interest.

In another embodiment, the invention provides a modified *Bacillus* host cell that comprises a vector comprising a polynucleotide construct that comprises a polynucleotide encoding a YmaH protein operably linked to a sigA and/or a sigH promoter polynucleotide sequence, wherein the modified cell is capable of producing a protein of interest chosen from amylases, proteases, xylanases, lipases, laccases, phenol oxidases, oxidases, cutinases, cellulases, hemicellulases, esterases, peroxidases, catalases, glucose oxidases, phytases, pectinases, glucosidases, isomerases, transferases, kinases phosphatases, galactosidases and chitinases, hormones, cytokines, growth factors, receptors, vaccines, and antibodies.

In another embodiment, the invention provides a modified *Bacillus* cell that comprises a vector comprising a polynucleotide construct that comprises a polynucleotide encoding a YmaH protein operably linked to a sigA and/or a sigH promoter polynucleotide sequence, wherein the modified cell is capable of producing an enzyme.

In another embodiment, the invention provides a modified *Bacillus* cell that comprises a vector comprising a polynucleotide construct that comprises a polynucleotide encoding a YmaH protein operably linked to a sigA and/or a sigH promoter polynucleotide sequence, wherein the modified cell is capable of producing a protease.

In another embodiment, the invention provides a modified *Bacillus* cell that comprises a vector comprising a polynucleotide construct that comprises a polynucleotide encoding a YmaH protein operably linked to a sigA and/or a sigH promoter polynucleotide sequence, wherein the modified cell is capable of producing at least one subtilisin chosen from subtilisin 168, subtilisin BPN', subtilisin Carlsberg, *B. lentus* subtilisin, *B. clausii* subtilisin, subtilisin DY, subtilisin 147 and subtilisin 309, and variants thereof.

In another embodiment, the invention provides a modified protease producing *Bacillus* cell that is capable of overexpressing ymaH, wherein the modified cell comprises a mutation in at least one gene chosen from degU, degQ, degS, sco4, spoIIE, degQ and degR.

In another embodiment, the invention provides a modified protease producing *Bacillus* cell that is capable of overexpressing ymaH, wherein the modified cell comprises a deg(Hy)32 mutation.

In another embodiment, the invention provides a modified protease producing *Bacillus subtilis* cell capable of overexpressing ymaH, wherein the modified cell comprises a mutation in at least one gene chosen from degU, degQ, degS, sco4, spoIIE, degQ and degR.

In another embodiment, the invention provides a method for obtaining a modified *Bacillus* cell, the method comprising transforming a *Bacillus* host cell with a vector comprising a polynucleotide construct that comprises a polynucleotide encoding a YmaH protein operably linked to a sigA and/or a sigH promoter polynucleotide sequence, wherein the *Bacillus* host cell is capable of expressing a protein of interest, and growing the modified *Bacillus* cell under suitable growth conditions for expressing the protein of interest.

In another embodiment, the invention provides a method for obtaining a modified *Bacillus* cell, the method comprising transforming a *Bacillus* host cell with a vector comprising a polynucleotide construct that is present on a replicating plasmid and that comprises a polynucleotide encoding a YmaH protein operably linked to a sigA and/or a sigH promoter polynucleotide sequence, wherein the *Bacillus* host cell is capable of expressing a protein of interest; and growing the modified *Bacillus* cell under suitable growth conditions for expressing the protein of interest.

In another embodiment, the invention provides a method for obtaining a modified *Bacillus* cell, the method comprising transforming a *Bacillus* host cell with a vector comprising a polynucleotide construct that is integrated into the genome of the modified cell and that comprises a polynucleotide encoding a YmaH protein operably linked to a sigA and/or a sigH promoter polynucleotide sequence, wherein the *Bacillus* host cell is capable of expressing a protein of interest; and growing the modified *Bacillus* cell under suitable growth conditions for expressing the protein of interest.

In another embodiment, the invention provides a method for obtaining a modified *Bacillus* cell, the method comprising transforming a *Bacillus* host cell with a vector comprising a polynucleotide construct that comprises a polynucleotide encoding a YmaH protein operably linked to a sigA and/or a sigH promoter polynucleotide sequence, wherein the *Bacillus* host cell is capable of expressing at least one subtilisin and growing the modified *Bacillus* cell under suitable growth conditions for expressing the subtilisin.

In another embodiment, the invention provides a method for producing a protein of interest in a modified *Bacillus* cell, the method comprising culturing the modified *Bacillus* cell that is capable of overexpressing ymaH, and growing the modified *Bacillus* cell under suitable growth conditions for expressing the protein of interest. In some embodiments, the protein of interest is an enzyme e.g. a subtilisin. In some embodiments, the *Bacillus* cell is a *Bacillus subtilis* cell.

In another embodiment, the invention provides a method for producing a protein of interest in a modified *Bacillus* cell, the method comprising culturing the modified *Bacillus* cell that is capable of overexpressing ymaH, growing the modified cell under suitable growth conditions for expressing the protein of interest, and recovering the protein of interest. In some embodiments, the protein of interest is an enzyme e.g. a subtilisin. In some embodiments, the *Bacillus* cell is a *Bacillus subtilis* cell.

In another embodiment, the invention provides a method for producing a protein of interest in a modified *Bacillus* cell at a time that is earlier than that at which the protein is produced in a corresponding precursor host cell, wherein the method comprises culturing the modified *Bacillus* cell that is capable of overexpressing ymaH, and growing the modified *Bacillus* cell under suitable growth conditions for expressing the protein of interest. In some embodiments, the protein of interest is an enzyme e.g. a subtilisin. In some embodiments, the *Bacillus* cell is a *Bacillus subtilis* cell.

In another embodiment, the invention provides a method for producing a protein of interest in a modified *Bacillus* cell, wherein an aprE promoter drives the expression of the protein of interest, and the method comprises culturing the modified *Bacillus* cell that is capable of overexpressing ymaH, and growing the modified cell under suitable growth conditions for expressing the protein of interest. In some embodiments, the protein of interest is an enzyme e.g. a subtilisin. In some embodiments, the *Bacillus* cell is a *Bacillus subtilis* cell.

In another embodiment, the invention provides a method for enhancing the expression of a protein of interest from *Bacillus*, wherein the methods comprise obtaining a modified *Bacillus* cell by using a method that comprises overexpressing ymaH in a *Bacillus* parent host cell, growing the resultant modified *Bacillus* cell under suitable growth conditions, and allowing the protein of interest to be expressed in the modified *Bacillus* cell, wherein the expression of the protein of interest in the modified *Bacillus* cell is enhanced when compared to the expression of the same protein of interest in the parent host cell. In some embodiments, the protein of interest is an enzyme e.g. a subtilisin. In some embodiments, the *Bacillus* cell is a *Bacillus subtilis* cell.

In another embodiment, the invention provides methods for enhancing the expression of a protein of interest from *Bacillus*, wherein the method comprises obtaining a modified *Bacillus* cell by a method that comprises overexpressing ymaH in a *Bacillus* parent host cell, growing the resultant modified *Bacillus* cell under suitable growth conditions, and allowing the protein of interest to be expressed in the modified *Bacillus* cell, wherein the expression of the protein of interest in the modified *Bacillus* cell is enhanced when compared to the expression of the same protein of interest in the parent host cell, and wherein overexpressing comprises transforming a *Bacillus* parent host cell with a polynucleotide construct comprising a polynucleotide encoding a YmaH protein, wherein the polynucleotide is operably linked to a sigA or a sigH promoter polynucleotide sequence. In some embodiments, the protein of interest is an enzyme e.g. a subtilisin. In some embodiments, the *Bacillus* cell is a *Bacillus subtilis* cell.

In another embodiment, the invention provides a method for enhancing the expression of a protein of interest from *Bacillus*, wherein the method comprises obtaining a modified *Bacillus* cell by a method that comprises overexpressing ymaH in a *Bacillus* parent host cell, growing the modified *Bacillus* cell under suitable growth conditions, and allowing the protein of interest to be expressed in the modified *Bacillus* cell, wherein the expression of the protein of interest in the modified cell is enhanced when compared to the expression of the same protein of interest in the parent host cell, and wherein overexpressing comprises transforming a *Bacillus* host cell with a polynucleotide construct that comprises a sequence chosen from SEQ ID NOS:1, 2, 3, and 13. In some embodiments, the protein of interest is an enzyme e.g. a subtilisin. In some embodiments, the *Bacillus* cell is a *Bacillus subtilis* cell.

In another embodiment, the invention provides a method for enhancing the expression of a protein of interest from *Bacillus*, wherein the method comprises obtaining a modified *Bacillus* cell by a method that comprises overexpressing ymaH in a *Bacillus* host cell, growing the modified *Bacillus* cell under suitable growth conditions, and allowing the protein of interest to be expressed in the modified *Bacillus* cell, wherein the expression of the protein of interest in the modified cell is enhanced when compared to the expression of the same protein of interest in the *Bacillus* host cell, and wherein overexpressing comprises transforming a *Bacillus* host cell with a polynucleotide construct that is present on a plasmid or is integrated into the genome of the modified cell and that comprises a polynucleotide encoding a YmaH protein, the polynucleotide being operably linked to a sigA or a sigH promoter polynucleotide sequence. In some embodiments, the protein of interest is an enzyme e.g. a subtilisin. In some embodiments, the *Bacillus* cell is a *Bacillus subtilis* cell.

In another embodiment, the invention provides a method for enhancing the expression of a protein of interest from *Bacillus*, wherein the method comprises obtaining a modified *Bacillus* cell by a method that comprises overexpressing ymaH in a wild-type *Bacillus* host cell, growing the modified *Bacillus* cell under suitable growth conditions, and allowing the protein of interest to be expressed in the modified *Bacillus* cell, wherein the expression of the protein of interest in the modified cell is enhanced when compared to the expression of the same protein of interest in the wild-type host cell, and wherein overexpressing comprises transforming a wild-type *Bacillus* host cell with a polynucleotide construct comprising a polynucleotide encoding a YmaH protein, the polynucleotide being operably linked to a sigA or a sigH promoter polynucleotide sequence. In some embodiments, the protein of interest is an enzyme e.g. a subtilisin. In some embodiments, the *Bacillus* cell is a *Bacillus subtilis* cell.

In another embodiment, the invention provides a method for enhancing the expression of a protein of interest from *Bacillus*, wherein the method comprises obtaining a modified *Bacillus* cell by a method that comprises overexpressing ymaH in an altered *Bacillus* host cell, growing the modified *Bacillus* cell under suitable growth conditions, and allowing the protein of interest to be expressed in the modified *Bacillus* cell, wherein the expression of the protein of interest in the modified *Bacillus* cell is enhanced when compared to the expression of the same protein of interest in the altered host cell, and wherein overexpressing comprises transforming an altered *Bacillus* host cell with a polynucleotide construct comprising a polynucleotide encoding a YmaH protein, the polynucleotide being operably linked to a sigA or a sigH promoter polynucleotide sequence. In some embodiments, the protein of interest is an enzyme e.g. a subtilisin. In some embodiments, the *Bacillus* cell is a *Bacillus subtilis* cell.

BRIEF DESCRIPTION OF THE DRAWINGS

FIG. 2 shows the polynucleotide sequence of a portion of the *B. subtilis* genome that comprises the sequence defining a sigA promoter to the end of the sequence encoding the YmaH protein. This sequence is diagrammed in FIG. 1, panel A. The beginning of the sequence encoding the miaA protein is indicated and the entire miaA coding sequence shown in bold letters; the beginning of sequence encoding the YmaH protein is indicated and the entire YmaH coding sequence shown in underlined bold letters.

FIG. 3 (A-B) Panel A shows a graph of the proteolytic activity of subtilisin produced by *Bacillus* control host cells (42pBS) and by modified *Bacillus* host cells that overexpress ymaH (42SigA1 and 42SigH). Panel B shows the subtilisin activity produced by *Bacillus* control host cells (41 pBS) and by modified *Bacillus* host cells that overexpress ymaH (41 SigH). The proteolytic activity was measured as the increase in absorbance at 405 nm due to the hydrolysis and release of p-nitroanaline. The level of enzymatic activity is indicative of the effect of overexpressing ymaH on the production of subtilisin by *Bacillus* host cells.

FIG. 4 shows the level of production of subtilisin by *Bacillus* control host cells 42pBS19 and by modified *Bacillus* host cells 42 SigH and 42SigA1, which overexpress ymaH.

DETAILED DESCRIPTION OF THE INVENTION

Figure 1:
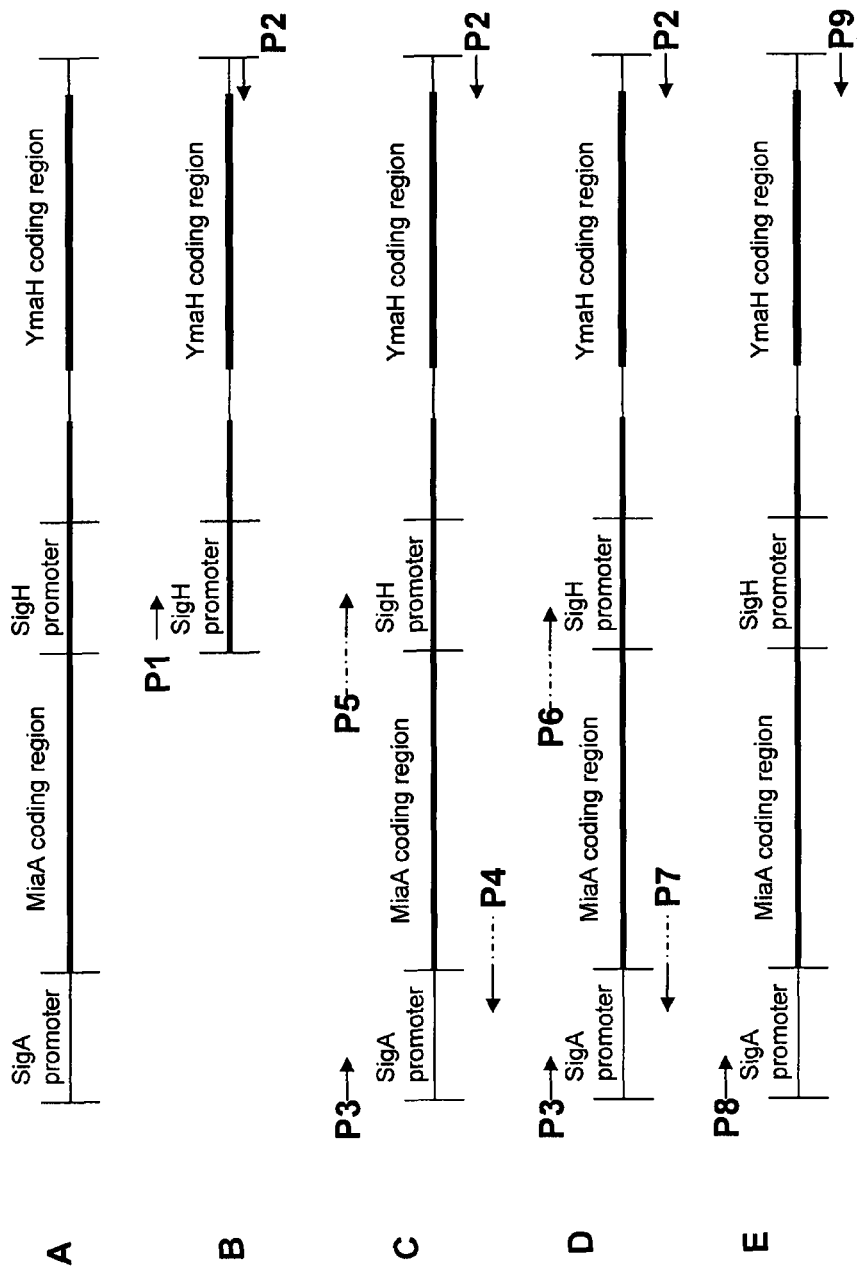
FIG. 1 (A-E) illustrates the location of primers used for generating polynucleotide constructs according to some embodiments of the present invention. Panels B-E show the position of the primers used to generate constructs SigH, SigA1, SigA2 and SigA3, respectively, relative to the *Bacillus* chromosomal sequence of the miaA operon of *Bacillus subtilis* (base pairs 1865428-1867019 of the *Bacillus subtilis* strain 168; NCBI accession number NC000964), which is illustrated in Panel A. Primer pairs P4-P5 and P6-P7 are fusion primers, which comprise a "tail" of base pairs at their 5' end that are homologous to the sequence being directly amplified, and are complementary to each other. The complementary tails of the fusion primers allow fusion of the amplified Sigma A promoter DNA to the amplified YmaH-encoding DNA to obtain chimeric polynucleotides containing the Sigma A promoter sequence adjacent to the YmaH-encoding sequence while deleting most, or all, of the miaA coding sequence.

The present invention relates to cells that have been genetically manipulated to have an altered capacity to express and/or produce proteins of interest. In particular, the present invention relates to modified host cells of Gram-positive microorganisms, such as *Bacillus* species that are capable of overexpressing ymaH. The invention encompasses polynucleotide constructs and expression vectors containing polynucleotide sequences that encode YmaH, and the modified host cells comprising them. In particular, the present invention relates to compositions and methods of overexpressing YmaH for enhancing the expression and production of proteins of interest (e.g., proteases) in *Bacillus* species.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and reagents described, as these may vary, depending upon the context they are used by those of skill in the art.

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

All patents, patent applications, and other publications, including all sequences disclosed within these references, referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

As used herein, the terms "isolated" and "purified" refer to a nucleic acid or amino acid (or other component) that is removed from at least one component with which it is naturally associated.

The terms "chimeric polynucleotide", "chimeric polynucleotide construct" and "heterologous nucleic acid construct" refer to a polynucleotide that is comprised of parts of different genes, including regulatory elements. Thus, in some embodiments, a chimeric polynucleotide construct comprises a protein coding region operably linked to a promoter that is not its native promoter. In some embodiments, a chimeric polynucleotide refers to a polynucleotide sequence that encompasses a polynucleotide sequence that defines a promoter and that is operably linked to a polynucleotide sequence that encodes a protein. In some embodiments, the promoter and the coding polynucleotides are contiguous.

The term "defining" in the context of a promoter refers to a polynucleotide sequence that comprises the promoter elements that enable transcription.

As used herein, the term "promoter" refers to a nucleic acid sequence that functions to drive/effect the transcription of a downstream gene. Typically, the promoter is appropriate to the host cell in which a gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, the upstream sequences of the upstream promoter elements (UP element) and enhancer or activator sequences. In some embodiments, the promoter also comprises a transcriptional leader sequence.

The terms "Sigma A promoter" and "SigA promoter" herein refer to the polynucleotide sequence comprising the core promoter sequences that include the sequences directly recognized by the corresponding $\sigma^A$ factor. The SigA promoter is encompassed by the sequence that naturally occurs upstream of the miaA coding region.

The terms "Sigma H promoter" and "SigH promoter" herein refer to the polynucleotide sequence comprising the core promoter sequences that include the sequences directly recognized by the corresponding σ factor. The SigH promoter is encompassed by the sequence that naturally occurs upstream of the ymaH coding region (Britton et al. J. Bacteriol. 184:4881-4890 [2002]). The core promoter comprises promoter sequences that include the sequences directly recognized by the corresponding σ factor and the spacer sequence located between the sequences directly recognized by the corresponding σ factor.

The term "aprE promoter" herein refers to the polynucleotide promoter sequence that naturally drives the expression of subtilisin in *B. subtilis* (Ferrari et al., J Bacteriol. 170:289-295 [1988]). In the context of aprE promoter, "an aprE promoter" herein refers to a wild-type aprE promoter and mutants thereof. In some embodiments, the aprE promoter includes the nucleotide sequences necessary for the transcriptional regulation exerted by DegU, ScoC, AbrB and any other regulator of such promoter, and/or the aprE transcriptional leader (Hambraeus et al., Microbiology 148:1795-1803 [2002]). In some alternative embodiments, the aprE promoter does not include all of the nucleotide sequences necessary for the transcriptional regulation exerted by DegU, ScoC, AbrB and other regulators, and/or does not include the aprE transcriptional leader sequence.

The terms "regulatory segment", "regulatory sequence", and "expression control sequence" refer to a polynucleotide sequence of DNA that is operatively linked with a polynucleotide sequence of DNA that encodes the amino acid sequence of a polypeptide chain to effect the expression of the encoded amino acid sequence. The regulatory sequence can inhibit, repress, or promote the expression of the operably linked polynucleotide sequence encoding the amino acid. In some embodiments, the regulatory sequence comprises a promoter that is operably linked to a DNA sequence that encodes the transcriptional regulator YmaH. In some embodiments the promoter is heterologous to the ymaH gene (e.g., the promoter is a promoter that does not immediately drive the expression of the YmaH protein). For example, in some embodiments, the promoter is a Sigma A promoter operably linked to the DNA that encodes the YmaH protein. In some other embodiments, the promoter is a promoter that immediately drives the expression of the YmaH protein and that is operably linked to the DNA encoding YmaH as it occurs in naturally occurring hosts.

The terms "polynucleotide" and "nucleic acid", used interchangeably herein, refer to a polymeric form of nucleotides of any length. These terms include, but are not limited to, a single-stranded DNA, double-stranded DNA, genomic DNA, cDNA, or a polymer comprising purine and pyrimidine bases, or other natural, chemically, biochemically modified, non-natural or derivatized nucleotide bases. Non-limiting examples of polynucleotides include genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. It will be understood that, as a result of the degeneracy of the genetic code, a multitude of nucleotide sequences encoding a given protein may be produced.

The term "gene" herein refers to a chromosomal segment of DNA involved in producing a polypeptide chain that may or may not include regions preceding and following the coding regions (e.g. 5' untranslated (5' UTR) or leader sequences and 3' untranslated (3' UTR) or trailer sequences, as well as intervening sequence (introns) between individual coding segments (exons)). In some embodiments, the gene encodes commercially important industrial proteins or peptides, such as enzymes including but not limited to proteases, cellulases, carbohydrases such as amylases and glucoamylases, cellulases, oxidases, isomerases, transferases, kinases, phosphatases and lipases. In some other embodiments, the gene encodes proteins encoded by the operon in which miaA occurs (e.g., miaA or ymaH). However, it is not intended that the present invention be limited to any particular enzyme or protein. In some other embodiments, the gene encodes other proteins or peptides, such as growth factors, cytokines, ligands, receptors and inhibitors, as well as vaccines and antibodies. In some embodiments, the gene of interest is a naturally-occurring gene, while in other embodiments, it is a mutated gene or a synthetic gene.

As used herein, "synthetic" refers to a polynucleotide molecule that is produced by in vitro chemical or enzymatic synthesis. It includes, but is not limited to variant nucleic acids made with optimal codon usage for host organisms, such as but not limited to Bacillus sp.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

The term "recombinant" refers to a polynucleotide or polypeptide that does not naturally occur in a host cell. In some embodiments, recombinant molecules comprise two or more naturally occurring sequences that are linked together in a way that does not occur naturally.

A nucleic acid is "operably linked" when it is placed into a functional relationship with another nucleic acid sequence. For example, a polynucleotide promoter sequence is operably linked to a polynucleotide encoding a polypeptide if it affects the transcription of the sequence. In some other embodiments, a ribosome binding site is operably linked to a coding sequence if it is positioned so as to facilitate translation. In some embodiments, "operably linked" means that the polynucleotide sequences being linked are contiguous. Linking is accomplished by ligation at convenient restriction sites. If such sites do not exist, synthetic oligonucleotide adapters or linkers are used in accordance with conventional practice.

As used herein, "homologous genes" refers to genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function in during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, an "analogous sequence" is one wherein the function of the gene is essentially the same as the gene designated from a preferred Bacillus subtilis strain (i.e. Bacillus subtilis 168). Additionally, analogous genes include at least about 60%, about 65%, about 70%, about 75%, about 80%, about 85%, about 90%, about 95%, about 97%, about 98%, about 99% or about 100% sequence identity with the sequence of the Bacillus subtilis strain 168 gene. Alternately, analogous sequences have an alignment of between 70 to 100% of the genes found in the B. subtilis 168 region and/or have at least between 5-10 genes found in the region aligned with the genes in the B. subtilis 168 genome. In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol. 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of a sequence disclosed herein. A preferred method utilizes the BLASTN module of WU-BLAST-2 set to the default parameters, with overlap span and overlap fraction set to 1 and 0.125, respectively.

In some embodiments, the alignment includes the introduction of gaps in the sequences to be aligned. In addition, for sequences which contain either more or fewer nucleotides than those of the candidate nucleic acid sequences, it is understood that the percentage of homology will be determined based on the number of homologous nucleotides in relation to the total number of nucleotides. Thus, for example, homology of sequences shorter than those of the sequences identified herein and as discussed below, will be determined using the number of nucleotides in the shorter sequence.

As used herein, "polynucleotide construct", "expression cassette," and "expression vector" refer to a DNA construct containing a DNA sequence that is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites and sequences which control termination of transcription and translation. Typically, the polynucleotide construct includes a transcriptional regulatory region (e.g., a promoter) operably linked to a protein coding region. In some embodiments, the polynucleotide construct comprises a protein coding region that is operably linked to a promoter that is its native promoter (i.e., the promoter is contiguous with to the coding sequence as found in nature). Thus, for example, a polynucleotide construct of the invention comprises a sigH promoter and a ymaH coding sequence. In other embodiments, the polynucleotide construct comprises a protein coding region that is operably linked to a promoter that is not its naturally contiguous promoter (i.e. the polynucleotide construct comprises a chimeric polynucleotide wherein the position of the promoter relative to the coding sequence in the construct is not that found in nature). For example, sigA promoter operably linked to a ymaH coding sequence. In other embodiments, the polynucleotide construct comprises more than one promoter and more than one protein coding region (e.g. the polynucleotide construct comprises a polycistronic sequence that comprises promoters and coding regions as found in an operon). In some other embodiments, the polynucleotide construct or expression cassette comprises a selective marker (e.g., an antibiotic resistance marker such as a gene coding for chloramphenicol acetyl transferase), which when in the presence of the appropriate antibiotic allows for the amplification of the polynucleotide construct in the genome of the host cell. The polynucleotide construct can be incorporated into a plasmid, genome, mitochondrial DNA, plastid DNA, virus or nucleic acid fragment. In some embodiments, the vector is a plasmid, a phage particle, or simply a potential genomic insert. In some additional embodiments, once transformed into a suitable host, the vector replicates and functions independently of the host genome, or, in some alternative instances, integrate into the genome itself. As used herein, "plasmid," "expression plasmid," and "vector" are often used interchangeably as the plasmid is the most commonly used form of vector at present. However, the invention is intended to include such other forms of expression vectors that serve equivalent functions and which are, or become, known in the art. "Vectors" include cloning vectors, expression vectors, shuttle vectors, plasmids, phage or virus particles, DNA constructs, cassettes and the like.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell. The term "plasmid" includes multicopy plasmids that can integrate into the genome of the host cell by homologous recombination.

As used herein, the terms "transformed" and "stably transformed" refer to a cell that has a non-native (heterologous) polynucleotide sequence integrated into its genome or comprises an episomal plasmid that is maintained for at least two or more generations. As used herein the term "expression" refers to a process by which a polynucleotide is transcribed and the resulting transcript is translated to yield a polypeptide. The process includes both transcription and translation.

The term "overexpression" herein refers to a process by which a gene comprising a sequence that encodes a polypeptide is artificially expressed in a modified cell to produce a level of expression of the encoded polypeptide that exceeds the level of expression of the same polypeptide in a precursor host cell. Thus, while the term is typically used in conjunction with a gene, the term "overexpression" may also be used in conjunction with a protein to refer to the increased level of a protein resulting from the overexpression of its encoding gene. In some embodiments, overexpression of a gene encoding a protein is achieved by increasing the number of copies of the gene that encodes the protein. In other embodiments, overexpression of a gene encoding a protein is achieved by increasing the binding strength of the promoter region and/or the ribosome binding site in such a way to increase the transcription and/or the translation of the gene that encodes the protein. In other embodiments, overexpression can be achieved by increasing the number of copies of a gene and increasing the binding strength of the promoter region and/or the ribosome binding site. In some embodiments, the overexpression of a gene encoding a protein results from the expression of at least one copy of the corresponding encoding polynucleotide present on a multicopy plasmid that has been introduced into a host cell. In other embodiments, the overexpression of a gene encoding a protein results from the expression of two or more copies of the corresponding encoding polynucleotide that are integrated into the genome of the host cell.

A "host cell" refers to a suitable cell from a cell that serves as a host for an expression vector comprising DNA according to the present invention. A suitable host cell may be a naturally occurring or wild-type host cell, or it may be an altered host cell. In one embodiment, the host cell is a Gram positive microorganism. In some preferred embodiments, the term refers to cells in the genus *Bacillus*.

As used herein, "a *Bacillus* cell" includes all members known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

A "wild-type host cell" is a host cell that has not been genetically altered using recombinant methods.

As used herein, the term "wild-type" refers to a gene or gene product which has the characteristics of that gene or gene product when isolated from a naturally occurring source. Typically, a wild-type gene is that which is most frequently observed in a population and is thus arbitrarily designed the "normal" or "wild-type" form of the gene. As used herein, the terms "wild-type sequence," and "wild-type gene" are used interchangeably and refer to a sequence that is native or naturally occurring in a host cell. The wild-type sequence may encode either a homologous or heterologous protein.

As used herein, "altered" host cell" "altered cell" and "altered strain" refer to a genetically engineered host cell (microorganism) wherein a protein of interest is expressed and/or produced at a level of expression or production that is greater than the level of expression and/or production of the same protein of interest in an unaltered or wild-type host cell grown under essentially the same growth conditions. In some embodiments, an altered host cell is a recombinant protease producing cell.

A "modified cell" and "modified host cell" herein refer to a wild-type or altered host cell that has been genetically engineered to overexpress a gene encoding a YmaH protein. In some embodiments, the modified host cell is a recombinant protease producing host cell. In some embodiments, the modified host cell is capable of expressing and/or producing a protein of interest at a greater level than its wild-type or altered parent host cell.

A "parent" or "precursor" cell herein refers to a cell from which a modified host cell is derived; the parent or precursor cell can be a wild-type cell or an altered cell. In some embodiments, an altered parent cell is capable of expressing and/or producing a protein of interest at levels that are greater than an unaltered or wild-type parent/precursor cell.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "*Genetics*," in Hardwood et al, (eds.), *Bacillus*, Plenum Publishing Corp., pages 57-72, [1989]).

As used herein, the terms "transformed" and "stably transformed" refer to a cell that has a non-native (heterologous) polynucleotide sequence integrated into its genome or has the heterologous polynucleotide sequence present as an episomal plasmid that is maintained for at least two generations.

As used herein, "transforming DNA/polynucleotide," "transforming sequence," and "DNA/polynucleotide construct" refer to DNA that is used to introduce sequences into a host cell or organism. "Transforming DNA" is DNA used to introduce sequences into a host cell or organism. The DNA may be generated in vitro by PCR or any other suitable techniques. In some preferred embodiments, the transforming DNA comprises an incoming sequence, while in other preferred embodiments it further comprises an incoming sequence flanked by homology boxes. In yet a further embodiment, the transforming DNA comprises other non-homologous sequences added to the ends (i.e., stuffer sequences or flanks). In some embodiments, the ends are closed, such that the transforming DNA forms a closed circle, such as, for example, insertion into a vector.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the term "selectable marker" refers to a gene capable of expression in host cell which allows for ease of selection of those hosts containing the vector. Examples of such selectable markers include but are not limited to antimicrobials, (e.g., kanamycin, erythromycin, actinomycin, chloramphenicol and tetracycline). Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. A "residing selectable marker" is one that is located on the genome of the microorganism to be transformed. A residing selectable marker encodes a gene that is different from the selectable marker on the transforming DNA construct.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both. Selection of cells by growth in the presence of a drug (e.g., an inhibitor of an inhibitable enzyme) may result in the amplification of either the endogenous gene encoding the gene product required for growth in the presence of the drug or by amplification of exogenous (i.e., input) sequences encoding this gene product, or both.

The term "polypeptide," as used herein, refers to a compound made up of amino acid residues linked by peptide bonds. In some embodiments, the term "protein" as used herein, is synonymous with the term "polypeptide". In some alternative embodiments it refers to a complex of two or more polypeptides. Thus, the terms "protein" and "polypeptide" are used interchangeably.

The term "YmaH protein" is interchangeably used with "Hfq protein" and refers to a protein that enhances the expression of a protein of interest. In the context of YmaH, "a YmaH protein" herein refers to a wild-type YmaH protein and variants thereof, including orthologs.

As used herein, "variant" refers to a protein which is derived from a precursor protein (e.g., a *B. subtilis* YmaH protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. A "*B. subtilis* YmaH protein" refers a *B. subtilis* YmaH protein modified as follows. The preparation of a *B. subtilis* YmaH protein variant is preferably achieved by modifying a DNA sequence which encodes for the native protein, transformation of that DNA sequence into a suitable host, and expression of the modified DNA sequence to form the derivative enzyme. The variant *B. subtilis* YmaH proteins of the invention include peptides comprising altered amino acid sequences in comparison with a precursor enzyme amino acid sequence wherein the variant *subtilis* YmaH protein retains the ability to enhance the production of a protein of interest in the *B. subtilis* cell in which the YmaH protein is overexpressed. The activity of the variant may be increased or decreased relative to the precursor secretion factor. It is contemplated that the variants according to the present invention may be derived from a DNA fragment encoding a *B. subtilis* YmaH protein variant wherein the functional activity of the expressed *B. subtilis* YmaH protein variant is retained.

A "protein of interest," and "polypeptide of interest," refer to the protein/polypeptide that is produced by a host cell. Generally, proteins of interest are desirable proteins that have commercial significance. The protein of interest may be either homologous or heterologous to the host. In some embodiments, the protein of interest is a secreted polypeptide, particularly an enzyme, including but not limited to amylolytic enzymes, proteolytic enzymes, cellulytic enzymes, oxidoreductase enzymes and plant wall degrading enzymes. In further embodiments, these enzyme include, but are not limited to amylases, proteases, xylanases, lipases, laccases, phenol oxidases, oxidases, cutinases, cellulases, hemicellulases, esterases, peroxidases, catalases, glucose oxidases, phytases, pectinases, glucosidases, isomerases, transferases, galactosidases and chitinases. In still further embodiments, the expressed polypeptide is a hormone, cytokine, growth factor, receptor, vaccine, antibody, or the like. While it is not intended that the present invention be limited to any particular protein/polypeptide, in some most preferred embodiments, the expressed protein of interest is a protease.

As used herein, the term "heterologous protein" refers to a protein or polypeptide that does not naturally occur in a host cell. Examples of heterologous proteins include enzymes such as hydrolases including proteases, cellulases, amylases, other carbohydrases, and lipases; isomerases such as racemases, epimerases, tautomerases, or mutases; transferases, kinases and phosphatases, In some embodiments, the proteins are therapeutically significant proteins or peptides, including but not limited to growth factors, cytokines, ligands, receptors and inhibitors, as well as vaccines and antibodies. In some alternate embodiments, the protein is a commercially important industrial protein or peptide (e.g., proteases, carbohydrases such as amylases and glucoamylases, cellulases, oxidases and lipases). In some embodiments, the gene encoding the proteins are naturally occurring genes, while in other embodiments, mutated and/or synthetic genes are used. In some embodiments, the gene encoding the proteins are naturally occurring genes, while in other embodiments, mutated and/or synthetic genes are used.

As used herein, the term "homologous protein" refers to a protein or polypeptide native or naturally occurring in a host cell. The present invention encompasses host cells producing the homologous protein via recombinant DNA technology. In alternative embodiments, the homologous protein is a native protein produced by other organisms, including but not limited to *E. coli*. The invention encompasses host cells producing the homologous protein via recombinant DNA technology. The present invention further encompasses a host cells with one or more deletions or one or more interruptions of the nucleic acid encoding the naturally occurring homologous protein or proteins, (e.g., a protease), and having nucleic acid encoding the homologous protein or proteins re-introduced in a recombinant form (i.e., in an expression cassette). In other embodiments, the host cell produces the homologous protein.

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology,* [1988]). For example, proteolytic activity may be ascertained by comparative assays which analyze the produced protease's ability to hydrolyze a commercial substrate. Exemplary substrates useful in the such analysis of protease or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference. The AAPF assay (See e.g., Del Mar et al., Anal. Biochem., 99:316-320 [1979]) also finds use in determining the production of mature protease. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration.

As used herein, the term "activity" refers to a biological activity associated with a particular protein, such as proteolytic activity associated with a protease. Biological activity refers to any activity that would normally be attributed to that protein by one skilled in the art.

The term "production" when in reference to a protein of interest encompasses the processing steps for the production of polypeptides, including the removal of the pro region, which typically creates the active mature form of the polypeptide that is known to occur during the maturation process. In some embodiments, the production of a polypeptide includes the removal of the signal peptide, which is known to occur during protein secretion (See e.g., Wang et al., Biochemistry 37:3165-3171 (1998); and Power et al., Proc Natl Acad Sci USA 83:3096-3100 [1986]). In some embodiments, the expressed protein is confined to the intracellular milieu of the cell in which it is expressed, while in other embodiments, the expressed protein is secreted to the extracellular environment. Thus, in some embodiments, the production of a protein of interest includes the cellular processes of expression of the protein and its secretion into the extracellular medium. For example, the production of a protease encompasses the two processing steps of a full-length protease including: 1. the removal of the signal peptide, which is known to occur during protein secretion; and 2. the removal of the pro region, which creates the active mature form of the enzyme and which is known to occur during the maturation process (Wang et al., Biochemistry 37:3165-3171 (1998); Power et al., Proc Natl Acad Sci USA 83:3096-3100 [1986]).

The term "early expression and/or early production" herein indicates that the expression and/or production of a protein of interest occurs in a host cell at a time that is earlier than that at which the protein of interest is normally expressed by the precursor/parent host. In some embodiments, the "early expression and/or production" of a protein of interest occurs earlier in a host that overexpresses YmaH than in a host cell that does not overexpress ymaH.

As used herein, the term "enhanced" refers to improved production of proteins of interest. In preferred embodiments, the present invention provides enhanced (i.e., improved) production of a protein of interest in a modified host. In these embodiments, the "enhanced" production is improved as compared to the normal levels of production by the unmodified wild-type or altered parent host (e.g., wild-type cells or altered cells that do not overexpress a transcriptional activator such as YmaH).

YmaH Polypeptides and Polynucleotide Constructs

In some embodiments, the invention provides polynucleotide constructs that comprise a promoter and a polynucleotide sequence that encodes a YmaH protein. The *B. subtilis* YmaH, also known as HFQ_BACSU is an RNA-binding protein, is a member of the Hfq family of RNA-binding proteins (Sauter et al., Nucleic Acid Res 31:4091-4098, [2003]). The YmaH protein is encoded in *Bacillus subtilis* by the ymaH gene, which is an ortholog of the hfq gene of *E. coli*. (Silvaggi et al., J Bacteriol. 187(19): 6641-6650, [2005]). YmaH is an abundant and ubiquitous RNA-binding protein that functions as a pleiotrophic regulator of RNA metabolism in prokaryotes, and is required for stabilization of some transcripts and degradation of others. YmaH binds preferentially to unstructured NU-rich RNA sequences and is similar to the eukaryotic Sm proteins in both sequence and structure. YmaH is also known to bind small RNA molecules called riboregulators that modulate the stability or translation efficiency of RNA transcripts.

The present invention provides methods and compositions for the overexpression of ymaH, which increases the production of a protein of interest in a host cell that has been modified to overexpress ymaH. In addition, as shown herein, overexpression of ymaH enhances the production of a protease in a *Bacillus* host cell. Overexpression of ymaH can be achieved by various means including enhancing the transcription and/or translation of the YmaH encoding polynucleotide. For example, at the transcriptional level, overexpression of ymaH can be achieved by increasing the number of polynucleotide sequences that encode ymaH in a host cell, and/or by increasing the binding strength of a ymaH promoter to enhance the activity of the cognate RNA polymerase. At the translational level, overexpression of ymaH can be achieved by enhancing the translational activity by mutating the ribosome binding site (RBS) to increase the affinity of ribosomes for the RBS. One skilled in the art will recognize that overexpression of ymaH can be effected by increasing the number of copies of the ymaH gene alone or in combination with other possible modifications made to the ymaH gene to achieve the overexpression of ymaH.

The invention provides for compositions including polynucleotide constructs, vectors and host cells that enable the overexpression of ymaH. The invention also provides methods for using the compositions of the invention to overexpress proteins of interest. The polynucleotide constructs of the invention comprise polynucleotide sequences that encode a YmaH protein and a SigA and/or a SigH promoter.

In one embodiment, the invention provides for the overexpression of ymaH by increasing the number of polynucleotide sequences that encode ymaH. Thus, the invention provides polynucleotide constructs comprising a polynucleotide sequence encoding ymaH operably linked to a ymaH promoter. A ymaH promoter can be any promoter that drives the expression of yamH (e.g., a SigA and/or a SigH promoter), and may be any nucleic acid sequence which shows transcriptional activity in the host cell of choice and includes mutant, truncated and hybrid promoters, and may be obtained from genes encoding extracellular or intracellular polypeptides either homologous or heterologous to the host cell. The promoter sequence may be native or foreign to the host cell.

In some embodiments, the promoter sequence may be obtained from a bacterial source. In some embodiments, the promoter sequence may be obtained from a Gram-positive bacterium such as a *Bacillus* strain (e.g., *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis*); or a *Streptomyces* strain (e.g., *Streptomyces lividans* or *Streptomyces murinus*); or from a gram negative bacterium (e.g., *E. coli* or *Pseudomonas* sp.)

The transcription of ymaH may be naturally driven by two promoters: a SigA promoter that is present upstream of miaA coding region, and the SigH promoter that is immediately upstream of the ymaH coding region in the miaA operon of *B. subtilis*. In some embodiments, the invention provides for polynucleotide constructs that comprise a polynucleotide sequence that encodes YmaH and a SigA promoter (e.g., SEQ ID NOs:2 and 3. SEQ ID NOs:2 and 3 exemplify embodiments wherein the ymaH coding sequence is contiguous with a SigA promoter sequence to provide a chimeric polynucleotide construct. In some preferred embodiments, chimeric polynucleotide constructs thus comprise a promoter sequence that in nature is not contiguous with the ymaH coding sequence. For example, SEQ ID NOS:2 and 3 exemplify chimeric constructs SigA1 and SigA2, respectively, which each comprise a SigA promoter that is operably linked to a polynucleotide sequence encoding ymaH.

(SEQ ID NO: 2)
GCGCCGAATTCTCATACCCTGAAAGGAAAGACAAGGGAAATTGTCGGCAA

TGAGCCGCTCGGCAGGTAGAAGGATGTTTACCGATGCAAAAAAGGGCAA

AATGGATAGGTGGTTGTCCATGTTGAATGCTATAATGGGGGAGATTTATA

AAAGAGAGTGATACATATTGAATAATACGAAGCAGCCCCACACATATAGC

AGGAAAACTCGAACTTTAATCGAAACTGTATGATATAGAGAATCAAGGAG

GACGAAACATGAAACCGATTAATATTCAGGATCAGTTTTTGAATCAAATC

CGGAAAGAAAATACGTATGTCACTGTTTTTTGCTGAACGGCTTTCAGTT

GCGGGGCCAGGTGAAAGGCTTTGATAACTTTACCGTATTGTTGGAATCGG

AAGGTAAGCAGCAGCTTATATATAAACATGCGATCTCAACGTTTGCGCCG

CAAAAAAACGTCCAGCTTGAACTCGAATAGATCAAAAAATGCCATGTCAA

GACATGAGGAAAGGCTGTCGGGGGTTCCCGGCGGCCATTTTTAACATGAA

TCCACTTTTGCTCCAAGCTTTTTGTGTAAGCTGACCATGCCAAGGCACGG

TCTTTTTTTATGAGGGATCCGGTGCC (SEQ ID NO: 3)
GCGCCGAATTCTCATACCCTGAAAGGAAAGACAAGGGAAATTGTCGGCAA

TGAGCCGCTCGGCAGGTAGAAGGATGTTTACCGATGCAAAAAAGGGCAA

AATGGATAGGTGGTTGTCCATGTTGAATGCTATAATGGGGGAGATTTATA

AAAGAGAGTGCTCGAACTTTAATCGAAACTGTATGATATAGAGAATCAAG

GAGGACGAAACATGAAACCGATTAATATTCAGGATCAGTTTTTGAATCAA

ATCCGGAAAGAAAATACGTATGTCACTGTTTTTTGCTGAACGGCTTTCA

GTTGCGGGGCCAGGTGAAAGGCTTTGATAACTTTACCGTATTGTTGGAAT

CGGAAGGTAAGCAGCAGCTTATATATAAACATGCGATCTCAACGTTTGCG

CCGCAAAAAAACGTCCAGCTTGAACTCGAATAGATCAAAAAATGCCATGT

CAAGACATGAGGAAAGGCTGTCGGGGGTTCCCGGCGGCCATTTTTAACAT

GAATCCACTTTTGCTCCAAGCTTTTTGTGTAAGCTGACCATGCCAAGGCA

CGGTCTTTTTTTATGAGGGATCCGGTGCC

In another embodiment, the invention provides polynucleotide constructs that comprise a polynucleotide sequence that encodes YmaH and a SigH promoter (e.g., SigH construct of SEQ ID NO:1, as shown below). SEQ ID NO:1 also exemplifies a polynucleotide construct that comprises a ymaH coding sequence that is naturally contiguous with a SigH promoter.

(SEQ ID NO: 1)
GGCACCGAATTCGACGTGGTTTCGCAACAAAATGCAGGTCACATGGTTCG

ATATGACACCGCCTGTTGATATGGAGCTGAAAAAAAAGGAAATTTTCACA

CATATAGCAGGAAAACTCGAACTTTAATCGAAACTGTATGATATAGAGAA

TCAAGGAGGACGAAACATGAAACCGATTAATATTCAGGATCAGTTTTTGA

ATCAAATCCGGAAAGAAAATACGTATGTCACTGTTTTTTGCTGAACGGC

TTTCAGTTGCGGGGCCAGGTGAAAGGCTTTGATAACTTTACCGTATTGTT

GGAATCGGAAGGTAAGCAGCAGCTTATATATAAACATGCGATCTCAACGT

TTGCGCCGCAAAAAAACGTCCAGCTTGAACTCGAATAGATCAAAAAATGC

CATGTCAAGACATGAGGAAAGGCTGTCGGGGGTTCCCGGCGGCCATTTTT

AACATGAATCCACTTTTGCTCCAAGCTTTTTGTGTAAGCTGACCATGCCA

AGGCACGGTCTTTTTTTATGAGGGATCCGGAGCC

In yet another embodiment, the invention provides for polynucleotide constructs that comprise a polynucleotide sequence that encodes YmaH and a SigA and a SigH promoter (e.g., SigA3 construct of SEQ ID NO: 13, as shown below).

(SEQ ID NO: 13)
TCATACCCTGAAAGGAAAGACAAGGGAAATTGTCGGCAATGAGCCGCTCG

GCAGGTAGAAGGATGTTTACCGATGCAAAAAAGGGCAAATGGATAGGT

GGTTGTCCATGTTGAATGCTATAATGGGGAGATTTATAAAAGAGAGTGA

TACATATTGAATAATACGAAGCAGCCCGTTGTCATTTTAGTCGGACCGAC

GGCAGTGGGGAAAACCAATTTAAGTATTCAGCTAGCCAAATCCTTAAACG

CGGAAATTATCAGCGGAGATTCGATGCAGATTTATAAAGGGATGGATATT

GGAACAGCTAAAATTACCGAACAGGAGATGGAGGGAGTGCCCCATCATCT

GATTGACATTTTAGATCCCCAAGACTCTTTCTCTACTGCCGATTATCAAA

GCTTAGTAAGAAATAAAATCAGCGAGATTGCAAATAGAGGAAAGCTTCCG

ATGATTGACGGCGGTACAGGGCTTTATATACAATCTGAGCTTTACGATTA

TACATTTACGGAAGAGGCAAATGATCCCGTGTTTCGAGAGAGCATGCAAA

TGGCTGCTGAGCGGGAAGGCGCTGACTTTCTTCATGCCAAACTTGCTGCA

GCAGATCCCGAGGCAGCAGCTGCGATTCATCCGAATAATACAAGAAGAGT

CATTCGCGCACTGGAAATTTTACATACGTCCGGAAAAACGATGTCCCAGC

```
-continued
ATTTGAAGGAACAAAAACGAGAACTTCTGTACAATGCAGTGTTAATTGGC

CTGACAATGGATAGAGACACGCTTTACGAAAGAATTAATCAGCGGGTCGA

TTTGATGATGCAGTCAGGCCTTCTTCCGGAAGTGAAACGCTTATACGACA

AGAACGTGAGAGACTGTCAATCAATACAGGCGATAGGCTATAAAGAGCTG

TATGCATATTTTGACGGTTTTGTGACACTTTCCGATGCTGTCGAACAGCT

AAAGCAGAACTCGAGGCGGTATGCGAAACGCCAGCTGACGTGGTTTCGCA

ACAAAATGCAGGTCACATGGTTCGATATGACACCGCCTGTTGATATGGAG

CTGAAAAAAAGGAAATTTTCACACATATAGCAGGAAAACTCGAACTTTA

ATCGAAACTGTATGATATAGAGAATCAAGGAGGACGAAACATGAAACCGA

TTAATATTCAGGATCAGTTTTTGAATCAAATCCGAAAGAAAATACGTAT

GTCACTGTTTTTTTGCTGAACGGCTTTCAGTTGCGGGGCCAGGTGAAAGG

CTTTGATAACTTTACCGTATTGTTGGAATCGGAAGGTAAGCAGCAGCTTA

TATATAAACATGCGATCTCAACGTTTGCGCCGCAAAAAAACGTCCAGCTT

GAACTCGAATAGATCAAAAAATGCCATGTCAAGACATGAGGAAAGGCTGT

CGGGGGTTCCCGGCGGCCATTTTTAACATGAATCCACTTTTGCTCCAAGC

TTTTTGTGTAAGCTGACCATGCCAAGGCACGGTCTTTTTTTATGAG
```

Examples of suitable promoters for directing the expression of the ymaH gene in are the SigA and the SigH promoters from the *B. subtilis* operon that encompasses the gene encoding miaA. For example, in one embodiment, the invention provides a polynucleotide sequence defining a SigA promoter (SEQ ID NO:14, as shown below).

```
                                      (SEQ ID NO: 14)
TCATACCCTGAAAGGAAAGACAAGGGAAATTGTCGGCAATGAGCCGCTCG

GCAGGTAGAAGGATGTTTACCGATGCAAAAAAAGGGCAAAATGGATAGGT

GGTTGTCCATGTTGAATGCTATAATGGGGGAGATTTATAAAAGAGAGTGA

TACATA
```

In another embodiment, the invention provides a polynucleotide sequence defining a SigH promoter (SEQ ID NO:16, as shown below).

```
                                      (SEQ ID NO: 16)
AAAGGAAATTTTCACACATATAGCAGGAAAACTCGAACTTTAATCGAAAC

TGTATGATATAGAGAATCAAGGAGGACGAAAC
```

Other examples of promoters that can be used for expressing the ymaH gene include Sigma A promoters that are recognized by $\sigma^A$ factor including the promoter of the *Streptomyces coelicolor* agarase gene (dagA), the promoter of the *Bacillus lentus* alkaline protease gene (aprH), the promoter of the *Bacillus licheniformis* alkaline protease gene (subtilisin Carlsberg gene), the promoter of the *Bacillus subtilis* levansucrase gene (sacB), the promoter of the *Bacillus subtilis* alpha-amylase gene (amyE), the promoter of the *Bacillus licheniformis* alpha-amylase gene (amyL), the promoter of the *Bacillus stearothermophilus* maltogenic amylase gene (amyM), and the promoter of the *Bacillus amtyloliquefacietis* alpha-amylase gene (amyQ). Examples of promoters that can be used for expressing the ymaH gene include Sigma H promoters that are recognized by $\sigma^H$ factors including spo0A, spo0F, spoVG and citG (See, Heimann, J. D. and C. P. Moran. 2002. RNA polymerase and sigma factors, pp 289-312 In A. L. Sonenshein, J. A. Hoch and R. Losick (ed), *Bacillus subtilis* and its closest relatives: from genes to cells. American Society for Microbiology, Washington, D.C.)

In some embodiments, a consensus SigA and/or SigH promoter finds use in the present invention. The construction of a consensus promoter may be accomplished by site-directed mutagenesis to create a promoter which conforms more perfectly to the established consensus sequences for the "−10" and "−35" regions of the vegetative "sigma A-type" promoters for *Bacillus subtilis* (Voskuil et al., Mol Microbiol 17: 271 279 [1995]). In other embodiments, a consensus promoter is created by site-directed mutagenesis to create a promoter which conforms more perfectly to the established consensus sequences for the "−10" and "−35" regions of the vegetative "sigma H-type" promoters for *Bacillus subtilis* (See, Helman and Moran in *Bacillus subtilis* and its closest relatives, Ch. 21, pg 289-312; Sonenshein et al (2002 ASM Press, Washington, D.C.) The consensus sequence for the "−35" region for the sigma A-type promoter is TTGaca and for the "−10" region is tgnTATaat, and the consensus sequence for the "−35" region for the sigma H-type promoter is RnAGGAwWW and for the "−10" region is RnnGAAT. Capital letters indicate highly conserved positions; lower case letters indicate less conserved positions; abbreviation R can be A or G, and W can be A or T. The consensus promoter may be obtained from any promoter which can function in a *Bacillus* host cell.

In some embodiments, the SigA promoter, which encompasses SEQ ID NO:14 is defined by a polynucleotide sequence that is naturally present upstream of the miaA coding sequence (SEQ ID NO:15, shown below), while the SigH promoter, which encompasses SEQ ID NO: 16, is defined by the polynucleotide sequence that is naturally present upstream of the yamH coding region (SEQ ID NO:17, shown below).

```
                                      (SEQ ID NO: 15)
TTGAATAATACGAAGCAGCCCGTTGTCATTTTAGTCGGACCGACGGCAGT

GGGGAAAACCAATTTAAGTATTCAGCTAGCCAAATCCTTAAACGCGGAAA

TTATCAGCGGAGATTCGATGCAGATTTATAAAGGGATGGATATTGGAACA

GCTAAAATTACCGAACAGGAGATGGAGGGAGTGCCCCATCATCTGATTGA

CATTTTAGATCCCCAAGACTCTTTCTCTACTGCCGATTATCAAAGCTTAG

TAAGAAATAAAATCAGCGAGATTGCAAATAGAGGAAAGCTTCCGATGATT

GACGGCGGTACAGGGCTTTATATACAATCTGAGCTTTACGATTATACATT

TACGGAAGAGGCAAATGATCCCGTGTTTCGAGAGAGCATGCAAATGGCTG

CTGAGCGGGAAGGCGCTGACTTTCTTCATGCCAAACTTGCTGCAGCAGAT

CCCGAGGCAGCAGCTGCGATTCATCCGAATAATACAAGAAGAGTCATTCG

CGCACTGGAAATTTTACATACGTCCGGAAAAACGATGTCCCAGCATTTGA

AGGAACAAAAACGAGAACTTCTGTACAATGCAGTGTTAATTGGCCTGACA

ATGGATAGAGACACGCTTTACGAAAGAATTAATCAGCGGGTCGATTTGAT

GATGCAGTCAGGCCTTCTTCCGGAAGTGAAACGCTTATACGACAAGAACG

TGAGAGACTGTCAATCAATACAGGCGATAGGCTATAAAGAGCTGTATGCA

TATTTTGACGGTTTTGTGACACTTTCCGATGCTGTCGAACAGCTAAAGCA

GAACTCGAGGCGGTATGCGAAACGCCAGCTGACGTGGTTTCGCAACAAAA

TGCAGGTCACATGGTTCGATATGACACCGCCTGTTGATATGGAGCTGAAA
```

-continued

AAAAAGGAAATTTTCACACATATAGCAGGAAAACTCGAACTTTAA (SEQ ID NO: 17)
ATGAAACCGATTAATATTCAGGATCAGTTTTTGAATCAAATCCGGAAAGA

AAATACGTATGTCACTGTTTTTTTGCTGAACGGCTTTCAGTTGCGGGCC

AGGTGAAAGGCTTTGATAACTTTACCGTATTGTTGGAATCGGAAGGTAAG

CAGCAGCTTATATATAAACATGCGATCTCAACGTTTGCGCCGCAAAAAAA

CGTCCAGCTTGAACTCGAATAG

The invention also encompasses promoter sequences that have been mutated to increase the activity of the promoter when compared to the activity of the corresponding wild-type promoter resulting in the overexpression of the YmaH protein. Thus, it is understood that variants of the sequences that define the SigA and SigH promoters find use in the constructs of the invention. Methods for creating promoter variants in Bacillus sp. are well known in the art (See e.g., Heimann et al., 2002. RNA polymerase and sigma factors, pp 289-312 In A. L. Sonenshein, J. A. Hoch and R. Losick (ed), Bacillus subtilis and its closest relatives: from genes to cells. American Society for Microbiology, Washington, D.C.) It is not intended that the present invention be limited to any particular promoter, as any suitable promoter known to those skilled in the art finds use with the present invention. Nonetheless, in some embodiments, the promoter is the B. subtilis sigH promoter, while in other embodiments, the promoter is the B. subtilis sigA promoter. In further embodiments, the sigH and the sigA promoters serve to effect the overexpression of YmaH protein.

In some embodiments, the polynucleotide constructs of the invention also comprise the requisite ribosome binding site to ensure optimal translation of the ymaH RNA transcript. In some embodiments, the polynucleotide construct comprises the ribosome bind site (RBS) sequence of the miaA gene (AAGAGAG; SEQ ID NO:21), while in other embodiments, polynucleotide construct comprises the RBS sequence of the ymaH gene (GGAGG; SEQ ID NO:22). In yet other embodiments, the polynucleotide construct comprises the ribosome binding site sequences of the miaA and the ymaH genes. In some embodiments, the invention provides constructs having the promoter and ribosome binding site sequences upstream of the ymaH coding sequence. The invention is not limited to the ribosome binding site sequences disclosed herein, as it also encompasses any suitable ribosome binding site sequences that have been mutated to increase the level of expression of the ymaH gene. Methods for obtaining mutated ribosome binding sequences that increase the expression of a gene in Bacillus are known in the art. For example, Band and Henner successfully increased the level of expression of Interferon in B. subtilis by modifying the RBS to obtain a tighter base-pairing to the 16S rRNA (Band, L. and D. J. Henner, DNA 3:17-21 [1984]).

The naturally-occurring YmaH protein from Bacillus subtilis is a 73 amino acid protein (SEQ ID NO:4) that is encoded by a 219 (222 including the stop codon) base pair polynucleotide (EMBL Primary Accession Number Z99113; SEQ ID NO:17).

(SEQ ID NO: 4)
MKPINIQDQFLNQIRKENTYVTVFLLNGFQLRGQVKGFDNFTVLLESEGK

QQLIYKHAISTFAPQKNVQLELE

Thus, in some embodiments, the polynucleotide construct sequence that encodes YmaH is the naturally-occurring polynucleotide sequence found in the genome of the wild-type Bacillus subtilis strain 168 (SEQ ID NO:4). The invention also encompasses variant YmaH proteins, including variant YmaH proteins that are derived from the wild-type protein by deletion (i.e. truncation), addition, or substitution of one or more amino acids at one or more sites in the native protein. Methods for such deletions, additions and substitutions are generally known in the art. For example, amino acid sequence variants of the polypeptide can be prepared by mutations in the cloned DNA sequence encoding the native protein of interest. Methods for mutagenesis and nucleotide sequence alterations are well known in the art (See, e.g., Kunkel (1985) Proc. Natl. Acad. Sci. USA 82:488 492; Kunkel et al. (1987) Methods Enzymol. 154:367 382; U.S. Pat. No. 4,873,192; and the references cited therein; herein incorporated by reference. In constructing variants of the proteins of interest, modifications to the nucleotide sequences encoding the variants will be made such that variants continue to possess the desired activity. As will be understood by the skilled artisan, due to the degeneracy of the genetic code, a variety of modified polynucleotides encode a YmaH protein. In some other embodiments of the present invention, polynucleotides comprising a nucleotide sequence having at least about 70% sequence identity, at least about 75% sequence identity, at least about 80% sequence identity, at least about 85% sequence identity, at least about 90% sequence identity, at least about 92% sequence identity, at least about 95% sequence identity, at least about 97% sequence identity, at least about 98% sequence identity, or at least about 99% sequence identity to the polynucleotide sequence of SEQ ID NO:17, are provided.

In other embodiments, the polynucleotide constructs of the invention comprise YmaH coding sequences that are analogous to the YmaH coding sequence of Bacillus subtilis strain 168. The genome of this strain, which is contained in one 4215 kb genome, has been well-characterized (See, Kunst et al., Nature 390:249-256 [1997]; and Henner et al., Microbiol. Rev., 44:57-82 [1980]). In some embodiments, the polynucleotide constructs of the invention comprise polynucleotide sequences that encode a YmaH protein that share at least about 65% amino acid sequence identity, at least about 70% amino acid sequence identity, at least about 75% amino acid sequence identity, at least about 80% amino acid sequence identity, at least about 85% amino acid sequence identity, at least about 90% amino acid sequence identity, at least about 92% amino acid sequence identity, at least about 95% amino acid sequence identity, at least about 97% amino acid sequence identity, at least about 98% amino acid sequence identity, and at least about 99% amino acid sequence identity with the amino acid sequence of the wild-type form of the YmaH protein and have comparable or improved ability to enhance the production of a protein of interest in a host cell when compared to the wild-type polypeptide (SEQ ID NO:4) and that retains the ability to enhance the expression of a protein of interest in a host cell. In yet other embodiments, the invention provides polynucleotide constructs comprising polynucleotide sequences that are homologous, orthologous or paralogous to genes of the wild-type Bacillus sequence of SEQ ID NO:17 and that retain the ability to enhance the production of a protein of interest.

The invention also encompasses polynucleotide constructs that comprise coding sequences encoding YmaH proteins that are related by being structurally and/or functionally similar. In some embodiments, these proteins are derived from a different genus and/or species, including differences between classes of organisms (e.g., a bacterial protein and a fungal protein). In some embodiments, these proteins are derived from a different genus and/or species. In additional embodiments, related proteins are provided from the same species. Indeed, it is not intended that the present invention be limited to related proteins from any particular source(s). In addition, the term "related proteins" encompasses tertiary structural homologs and primary sequence homologs (e.g., the YmaH of the present invention). For example, the present invention encompasses such homologues including but not limited to such YmaH proteins as the YmaH of *E. coli*, (HFQ_ECOLI), *Shighella flexneri* (HFQ_SHIFL), *Salmonella typhimurium* (HFQ_SALTY), *Yersinia enterocolitica* (HFQ_YEREN), *Yersinia pestis* (HFQ_YERPE), *Erwinia carotovora* (HFQ_ERWCA), *Haemophilus influenzae* (HFQ_HAEIN), *Pasteurella multocida* (HFQ_PASMU), *Vibrio cholerae* (HFQ_VIBCH), *Pseudomonas aeruginosa* (HFQ_PSEAE), *Xanthomonas axonopodis* (HFQ_XANAC), *Xanthomonas campestris* (HFQ_XANCP), *Xylella fastidiosa* (GSQ_XYLFA), *Neisseria meningitidis* (HFQ_NEIMA), *Ralstonia solanacearum* (HFQ_RALSO), *Agrobacterium tumefaciens* (HFQ_AGRTS), *Brucella melitensis* (HFQ_BRUME), *Rhizobium loti* (HFQ_RHILO), *Azorhizobium caulinodans* (HFQ_AZOCA), *Caulobacter crescentus* (HFQ_CAUCR), *Aquifex melitensis* (HFQ_AQUAE), *Thermotoga maritime* (HFQ_THEMA), *Clostridium acetobutylicum* (HFQ_CLOAB), *Clostridium perfringens* (HFQ_CLOPE), *Bacillus halodurans* (HFQ_BACHD), *Bacillus subtilis* (HFQ_BACSU), *Thermoanaerobacter tengcongensis* (HFQ_THETN), *S. aureus* (Q99UG9), and *M. jannasci* (Q58830) (Sauter et al., Nucleic Acids Res. 31:4091-4098 [2003]).

Related (and derivative) proteins comprise variant YmaH proteins. In some preferred embodiments, variant proteins differ from a parent protein and one another by a small number of amino acid residues. The number of differing amino acid residues may be one or more, preferably about 1, 2, 3, 4, 5, 10, 15, 20, 30, 40, 50, or more amino acid residues. In some preferred embodiments, the number of different amino acids between variants is between about 1 and about 10. In some particularly preferred embodiments, related proteins and particularly variant proteins comprise at least about 70%, about 75%, about 80%, about 85%, about 90%, about 95%, about 97%, about 98%, or about 99% amino acid sequence identity. Several methods are known in the art that are suitable for generating variants of the YmaH proteins of the present invention, including but not limited to site-saturation mutagenesis, scanning mutagenesis, insertional mutagenesis, random mutagenesis, site-directed mutagenesis, and directed-evolution, as well as various other recombinatorial approaches.

Characterization of wild-type and mutant proteins is accomplished via any means suitable and is preferably based on the assessment of properties of interest. For example, it is contemplated that YmaH proteins that are capable of enhancing the production of a protein of interest will find use.

In certain embodiments, the recombinant polynucleotides of the invention comprise a polynucleotide sequence that may be codon optimized for expression of a YmaH protein in the host cell used. Since codon usage tables listing the usage of each codon in many cells are known in the art (See, e.g., Nakamura et al., Nucl. Acids Res., 28:292 [2000]) or readily derivable, such nucleic acids can be readily designed giving the amino acid sequence of a protein to be expressed. In some embodiments, the codon-optimized sequence comprises a polynucleotide that encodes a YmaH protein that is at least about 70% identical to SEQ ID NO:4.

ymaH Vectors

The invention provides vectors comprising the polynucleotide constructs of the invention. The vectors are introduced into a host cell to overexpress the YmaH protein.

In some embodiments, the overexpression of a polypeptide results from the expression of one or more copies of the corresponding YmaH-encoding polynucleotide that is present on a multicopy/replicating plasmid that has been introduced into a host cell. Thus, in some embodiments, the invention provides for a vector comprising a polynucleotide construct that is incorporated into the vector. In some embodiments, the vector is a multicopy/replicating plasmid vector which forms an extrachromosomal self-replicating genetic element that overexpresses YmaH in the host cell. Typically, the vector is a plasmid vector, which carries a selectable marker gene that allows for ease of selecting the host cells that contain the plasmid. Vectors that replicate autonomously in a host cell include vectors that comprise an origin of replication, which enables the vector to replicate autonomously in the *Bacillus* cell. Examples of bacterial origins of replication are the origins of replication of plasmids pBR322, pUC19, pACYC177, and pACYC184 permitting replication in *E. coli*, and pUB110, pC194, pE194, pTA1060, and pAM61 permitting replication in *Bacillus*. The origin of replication may be one having a mutation to make its function temperature-sensitive in the *Bacillus* cell (See, e.g., Ehrlich, Proceedings of the National Academy of Sciences USA 75:1433 [1978]).

As indicated above, in some embodiments of the present invention, a polynucleotide encoding YmaH protein is introduced into a host cell via an expression vector capable of replicating within the host cell. Suitable replicating and integrating plasmids for *Bacillus* known in the art (See e.g., Harwood and Cutting (eds), *Molecular Biological Methods for Bacillus*, John Wiley & Sons, [1990], in particular, chapter 3; suitable replicating plasmids for *B. subtilis* include those listed on page 92).

In some embodiments, the overexpression of a YmaH polypeptide results from the expression of at least one copy of a YmaH-encoding polynucleotide that is integrated into the genome of the host cell. Thus, in some embodiments, when the vector is introduced into the host cell, it is integrated into the genome and replicated together with the genome into which it has integrated. Multiple copies of the ymaH gene can be integrated at several positions in the genome of the host cell. Alternatively, an amplifiable expression cassette carrying a sequence encoding YmaH and a selectable marker (e.g., an antimicrobial resistance marker, such as a gene coding chloramphenicol acetyl transferase) can be integrated in the genome via a single cross-over event and then amplified by challenging the transformed host cell with increasing concentrations of the appropriate antimicrobial (e.g., chloramphenicol).

In other embodiments, the invention provides a polynucleotide construct that is incorporated into an integrating vector. In some embodiments, the polynucleotide constructs of the invention that are incorporated into an integrating vector are targeted to chromosomal sequences of the *Bacillus* host cell to create modified host cells that comprise stable tandem integrations of multiple vector copies. The polynucleotide construct that is incorporated into the integration vector typically comprises a selectable marker gene that provides the cell with resistance to an antimicrobial agent and allows for the amplification of the integrated ymaH construct. Tandem integration into a single site as well as single-copy and two-site integration may occur. Whether the polynucleotide construct is incorporated into a vector or used without the presence of plasmid DNA, it is used to transform host cells using any suitable method known in the art.

Methods for introducing DNA into *Bacillus* cells involving plasmid constructs and transformation of plasmids into bacterial host cells are well known. In some embodiments, the plasmids are subsequently isolated from *E. coli* and transformed into *Bacillus*. However, it is not essential to use intervening microorganisms such as *E. coli*, and in some embodiments, a DNA construct or vector is directly introduced into a *Bacillus* host.

Those of skill in the art are well aware of suitable methods for introducing polynucleotide sequences into *Bacillus* cells (See e.g., Ferrari et al., "Genetics," in Harwood et al. (ed.), *Bacillus*, Plenum Publishing Corp. [1989], pages 57-72; Saunders et al., J. Bacteriol., 157:718-726 [1984]; Hoch et al., J. Bacteriol., 93:1925-1937 [1967]; Mann et al., Current Microbiol., 13:131-135 [1986]; and Holubova, Folia Microbiol., 30:97 [1985]; Chang et al., Mol. Gen. Genet., 168:11-115 [1979]; Vorobjeva et al., FEMS Microbiol. Lett., 7:261-263 [1980]; Smith et al., Appl. Env. Microbiol., 51:634 [1986]; Fisher et al., Arch. Microbiol., 139:213-217 [1981]; and McDonald, J. Gen. Microbiol., 130:203 [1984]). Indeed, such methods as transformation, including protoplast transformation and congression, transduction, and protoplast fusion are known and suited for use in the present invention. Methods of transformation are particularly preferred to introduce a DNA construct provided by the present invention into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell without insertion into a plasmid or vector. Such methods include, but are not limited to electroporation, insertion of naked DNA or liposomes and the like. In additional embodiments, DNA constructs are co-transformed with a plasmid, without being inserted into the plasmid. In further embodiments, a selective marker is deleted from the altered *Bacillus* strain by methods known in the art (See, Stahl et al., J. Bacteriol., 158:411-418 [1984]; and Palmeros et al., Gene 247:255-264 [2000]).

Methods known in the art to transform *Bacillus*, include such methods as plasmid marker rescue transformation, which involves the uptake of a donor plasmid by competent cells carrying a partially homologous resident plasmid (Contente et al., Plasmid 2:555-571 [1979]; Haima et al., Mol. Gen. Genet., 223:185-191 [1990]; Weinrauch et al., J. Bacteriol., 154:1077-1087 [1983]; and Weinrauch et al., J. Bacteriol., 169:1205-1211 [1987]). In this method, the incoming donor plasmid recombines with the homologous region of the resident "helper" plasmid in a process that mimics chromosomal transformation.

Other methods involving transformation by protoplast transformation are well known in the art (See e.g., Chang and Cohen, Mol. Gen. Genet., 168:111-115 [1979]; Vorobjeva et al., FEMS Microbiol. Lett., 7:261-263 [1980]; Smith et al., Appl. Env. Microbiol., 51:634 [1986]; Fisher et al., Arch. Microbiol., 139:213-217 [1981]; McDonald [1984] J. Gen. Microbiol., 130:203 [1984]; and Bakhiet et al., 49:577 [1985]). In addition, Mann et al., (Mann et al., Curr. Microbiol., 13:131-135 [1986]) describe transformation of *Bacillus* protoplasts, and Holubova (Holubova, Microbiol., 30:97 [1985]) describe methods for introducing DNA into protoplasts using DNA-containing liposomes. In some embodiments, marker genes are used in order to indicate whether or not the gene of interest is present in the host cell. In some embodiments, the ymaH polynucleotide sequence contained in the vector of the invention encodes for a YmaH protein having SEQ ID NO:4 or variants thereof.

In addition to these methods, in other embodiments, host cells are directly transformed. In "direct transformation," an intermediate cell is not used to amplify, or otherwise process, the modified polynucleotide prior to introduction into the host (i.e., *Bacillus*) cell. Introduction of the modified polynucleotide into the host cell includes those physical and chemical methods known in the art to introduce modified polynucleotide into a host cell without insertion into a plasmid or vector. Such methods include but are not limited to the use of competent cells, as well as the use of "artificial means" such as calcium chloride precipitation, electroporation, etc. to introduce DNA into cells. Thus, the present invention finds use with naked DNA, liposomes and the like. In yet other embodiments, the modified polynucleotides are co-transformed with a plasmid without being inserted into the plasmid. In some embodiments, the invention provides a vector containing a polynucleotide encoding a YmaH protein operably linked to a sigA promoter (e.g., SEQ ID NO:2 and 3). In other embodiments, the vector contains a YmaH encoding polynucleotide operably linked to a sigH promoter (e.g., SEQ ID NO:1). In yet other embodiments, the vector comprises a polynucleotide construct that contains a YmaH coding sequence, a sigA promoter and a sigH promoter (e.g., SEQ ID NO: 13).

In some embodiments, ymaH is overexpressed by a non-integrating vector. In some embodiments, ymaH is overexpressed in a host cell in which one or more chromosomal genes have been modified (e.g., degU) and/or deleted (e.g., nprE) from the *Bacillus* genome. In some further embodiments, one or more indigenous chromosomal regions have been modified and/or deleted from a corresponding wild-type *Bacillus* host genome. In some preferred embodiments, the present invention provides methods and compositions for the improved expression and/or secretion of at least one protein of interest by *Bacillus*.

ymaH Host Cells

The present invention provides modified host cells that have been genetically manipulated to overexpress ymaH and have an enhanced capacity to produce proteins of interest. In particular, the present invention relates to modified host cells of Gram-positive microorganisms, such as *Bacillus* species that overexpress ymaH. In some embodiments, ymaH is overexpressed in wild-type microorganisms, while in other embodiments, YmaH is overexpressed in altered host cells. In some embodiments, the altered host cell is capable of producing a protein of interest at a level that is greater than that of its wild-type precursor. In some particularly preferred embodiments overexpression of YmaH in the overproducing altered parent hosts further increases the level of production of the protein of interest. In some embodiments, overexpression of YmaH in an altered parent host induces production of a protein of interest at an earlier time than production would occur in the corresponding unaltered parent host. Overexpression of ymaH in a host cell is obtained using the vectors and constructs of the invention as described herein. Thus, in some embodiments, the invention provides for a modified host cell that is obtained by transforming a wild-type or an altered host cell with a vector that comprises a YmaH coding sequence operably linked to a sigA and/or sigH promoter. In particular, the modified host cells of the invention are capable of producing a protein of interest and in some embodiments, the modified host cells comprises polynucleotide constructs that encode YmaH (e.g., SEQ ID NOS:1, 2, 3, or 13).

In some embodiments, the invention provides methods for overexpressing ymaH in a host cell to increase the production of a protein of interest. The protein of interest may be either homologous or heterologous to the host. In some embodiments, the protein of interest is a secreted polypeptide, particularly an enzyme including but not limited to amylolytic enzymes, proteolytic enzymes, cellulytic enzymes, oxidoreductase enzymes and plant wall degrading enzymes. In further embodiments, these enzyme include, but are not limited to amylases, proteases, xylanases, lipases, laccases, phenol oxidases, oxidases, cutinases, cellulases, hemicellulases, esterases, peroxidases, catalases, glucose oxidases, phytases, pectinases, glucosidases, isomerases, transferases, kinases phosphatases, galactosidases and chitinases. In still further embodiments, the protein of interest is a hormone, cytokine, growth factor, receptor, vaccine, antibody, or the like. While it is not intended that the present invention be limited to any particular protein, in some embodiments, the protein of interest is a protease.

In some embodiments, the host cells are *Bacillus* sp., *Streptomyces* sp., *Escherichia* sp. or *Aspergillus* sp. In other embodiments, the proteins of interest are proteases that are produced by host cells of the genus *Bacillus* (See e.g., U.S. Pat. No. 5,264,366, U.S. Pat. No. 4,760,025, and RE 34,6060). In some embodiments, the *Bacillus* strain of interest is an alkalophilic *Bacillus*. Numerous alkalophilic *Bacillus* strains are known (See e.g., U.S. Pat. No. 5,217,878; and Aunstrup et al., Proc IV IFS: Ferment. Tech. Today, 299-305 [1972]). Another type of *Bacillus* strain of particular interest is a cell of an industrial *Bacillus* strain. Examples of industrial *Bacillus* strains include, but are not limited to *B. licheniformis*, *B. lentus*, *B. subtilis*, *B. clausii*, and *B. amyloliquefaciens*. In additional embodiments, the *Bacillus* host strain is selected from the group consisting of *B. licheniformis*, *B. subtilis*, *B. lentus*, *B. brevis*, *B. stearothermophilus*, *B. alkalophilus*, *B. amyloliquefaciens*, *B. coagulans*, *B. circulans*, *B. lautus*, *B. pumilus*, *B. thuringiensis*, and *B. megaterium* as well as other organisms within the genus *Bacillus*. In preferred embodiments, *B. subtilis* cells are used.

In some embodiments, the industrial host strains are selected from the group consisting of non-recombinant strains of *Bacillus* sp., mutants of a naturally-occurring *Bacillus* strain, and recombinant *Bacillus* host strains. Preferably, the host strain is a recombinant host strain, wherein a polynucleotide encoding a polypeptide of interest has been previously introduced into the host. A further preferred host strain is a *Bacillus subtilis* host strain, and particularly a recombinant *Bacillus subtilis* host strain. Numerous *B. subtilis* strains are known and suitable for use in the present invention (See e.g., 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain; Hoch et al., Genetics, 73:215-228 [1973]; U.S. Pat. No. 4,450,235; U.S. Pat. No. 4,302,544; EP 0134048). The use of *B. subtilis* as an expression host is well known in the art (See Palva et al., Gene, 19:81-87 [1982]; Fahnestock and Fischer, J. Bacteriol., 165:796-804 [1986]; and Wang et al, Gene 69:39-47 [1988]).

Of particular interest as host cells are cells of industrial protease-producing *Bacillus* strains. By using these strains, the high efficiency of protease production is further enhanced by the use of modified *Bacillus* strains provided by the present invention. Industrial protease producing *Bacillus* strains provide particularly preferred expression hosts. In some embodiments, use of these strains in the present invention provides further enhancements in protease production. As indicated above, there are two general types of proteases are typically secreted by *Bacillus* sp., namely neutral (or "metalloproteases") and alkaline (or "serine") proteases. Also as indicated above, subtilisin is a preferred serine protease for use in the present invention. A wide variety of *Bacillus* subtilisins have been identified and sequenced, for example, subtilisin 168, subtilisin BPN', subtilisin Carlsberg, subtilisin DY, subtilisin 147, subtilisin 309 (See e.g., EP 414279 B; WO 89/06279; and Stahl et al., J. Bacteriol., 159:811-818 [1984]), *B. lentus* subtilisin, and *B. clausii* subtilisin, (J C van der Laan, G Gerritse, L J Mulleners, R A van der Hoek and W J Quax. Appl Environ Microbiol. 57: 901-909 [1991]).

In some embodiments of the present invention, the *Bacillus* host strains produce mutant (e.g., variant) proteases. Numerous references provide examples of variant proteases and reference (See e.g., WO 99/20770; WO 99/20726; WO 99/20769; WO 89/06279; RE 34,606; U.S. Pat. No. 4,914,031; U.S. Pat. No. 4,980,288; U.S. Pat. No. 5,208,158; U.S. Pat. No. 5,310,675; U.S. Pat. No. 5,336,611; U.S. Pat. No. 5,399,283; U.S. Pat. No. 5,441,882; U.S. Pat. No. 5,482,849; U.S. Pat. No. 5,631,217; U.S. Pat. No. 5,665,587; U.S. Pat. No. 5,700,676; U.S. Pat. No. 5,741,694; U.S. Pat. No. 5,858,757; U.S. Pat. No. 5,880,080; U.S. Pat. No. 6,197,567; and U.S. Pat. No. 6,218,165.

In some embodiments, the expression of the protein of interest in a host cell is driven by the aprE promoter of the aprE gene from which the *B. subtilis* subtilisin is naturally transcribed. The aprE gene is transcribed by sigma A ($\sigma^A$) factor and its expression is highly controlled by several regulators, such as: DegU/DegS, AbrB, Hpr and SinR (Valle and Ferrari (1989) In: Smith I, Slepecky R A, Setlow P (eds) Regulation of Procaryotic Development. American Society for Microbiology. Washington, D.C. pp 131-146), and a consensus Sigma A promoter has been identified TGGGTCT-TGACAAATATTATTCCATCTATTA-CAATAAATTCACAGA (SEQ ID NO:23; US 2003014846; Helman et al., 1995, Nucleic Acid Research, Vol. 24, pp. 2351-2360). In some embodiments, the host cell comprises an aprE promoter that is the wild-type aprE promoter TGGGTCTACTAAAATATTATTCCATC-TATTACAATAAATTCACAGA (SEQ ID NO:24; U.S. Patent Application Publication No. 20030148461).

In other embodiments, the expression of a protein of interest by a host cell is driven by mutant of the *B. subtilis* aprE promoters. In some embodiments, the invention provides for a *Bacillus* host cell that contains a mutant aprE promoter operably linked to a polynucleotide sequence that encodes a protein of interest. Thus, the invention encompasses host cells that express a protein of interest from a mutant aprE promoter. An example of a mutant aprE promoter is the mutant aprE promoter having the sequence TGGGTC TTGACA AATAT-TATTCCATCTAT TACAAT AAATTCACAGA (SEQ ID NO: 25), which is described in U.S. Patent Application Publication No. 20030148461. Any one of the proteins of interest recited herein (e.g., *Bacillus* subtilisins) can be transcribed from an aprE promoter. In some embodiments, the invention provides for a modified *Bacillus* host cell that is capable of expressing a protein of interest from an aprE promoter. In some embodiments, the modified host cell is a modified *B. subtilis* host cell capable of expressing a protease driven by an aprE promoter. In some embodiments, the aprE promoter includes the aprE promoter regulatory elements and/or the aprE transcriptional leader, while in other embodiments, the aprE promoter does not include the aprE promoter regulatory elements and/or the aprE transcriptional leader.

In addition to the aprE promoter, the invention also encompasses compositions and methods for expressing a protein of interest by a host cell, wherein the expression of the gene encoding the protein of interest is driven by any promoter suitable for driving the transcription of the gene of interest as long as the promoter comprises the transcriptional leader sequence of the aprE gene.

In another embodiment, a *Bacillus* host is a *Bacillus* sp. that includes a mutation or deletion in at least one of the degU, degS, degR and/or degQ genes. Preferably the mutation is in a degU gene, and more preferably the mutation is degU(Hy) 32. (See, Msadek et al., J. Bacteriol., 172:824-834 [1990]; and Olmos et al., Mol. Gen. Genet., 253:562-567 [1997]). A most preferred host strain is a *Bacillus subtilis* carrying a degU(Hy)32 mutation. In a further embodiment, the *Bacillus* host comprises a mutation or deletion in scoC4, (See, Caldwell et al., J. Bacteriol., 183:7329-7340 [2001]); and spoIIE (See, Arigoni et al., Mol. Microbiol., 31:1407-1415 [1999]); In some embodiments, these mutations occur alone, while in other embodiments, combinations of mutations are present. In some embodiments, a modified *Bacillus* of the invention is obtained from a *Bacillus* host strain that already includes a mutation in one or more of the above-mentioned genes. In some embodiments, an altered *Bacillus* host that has an enhanced capacity to produce a protein of interest is selected as the host cell of the invention. In some embodiments, the altered *Bacillus* host cell has an enhanced capacity to produce a protease.

Culturing Methods

The invention provides methods for producing a protein of interest in a modified *Bacillus* cell that is capable of overexpressing ymaH by culturing the modified cell that is capable of producing a protein of interest and growing the cell under suitable growth conditions for expressing the protein of interest. In some embodiments, the host cells and modified host cells of the present invention are cultured in conventional nutrient media. The suitable specific culture conditions, such as temperature, pH and the like are known to those skilled in the art. Additional preferred culture conditions are well known to those of skill in the art and are described in various reference publications.

In some embodiments, the protein of interest produced by the modified host cell is confined to the intracellular milieu of the host cell, while in other embodiments, the protein of interest produced by the host cell is secreted into the extracellular space (i.e. the culture medium). Thus, in some embodiments, the protein of interest can be recovered from the intracellular milieu of the cell in which it is expressed by lysing the host cell and recovering the protein of interest by methods known in the art. In other embodiments, modified host cells are cultured under conditions suitable for the expression and recovery of the protein of interest from the cell culture. The protein of interest produced by a modified host cell overexpressing ymaH according to the present invention is secreted into the culture media. In some embodiments, the protein of interest (e.g., a protease), produced by the cells is recovered from the culture medium by conventional procedures, including, but not limited to separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Thus, any method suitable for recovering the protease(s) of the present invention finds use in the present invention. Indeed, it is not intended that the present invention be limited to any particular purification method.

In some embodiments, other recombinant constructions join the heterologous or homologous polynucleotide sequences encoding the proteins of interest to nucleotide sequence encoding a polypeptide domain which facilitates purification of soluble proteins (Kroll D J et al., DNA Cell Biol 12:441-53 [1993]). Such purification facilitating domains include, but are not limited to, metal chelating peptides such as histidine-tryptophan modules that allow purification on immobilized metals (Porath, Protein Expr Purif 3:263-281 [1992]), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein also find use to facilitate purification.

In some embodiments, the transformed host cells of the present invention are cultured in a suitable nutrient medium under conditions permitting the expression of a protein of interest (e.g., a protease), after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (e.g., in catalogues of the American Type Culture Collection). In some embodiments, the host cells are cultured under batch, fed-batch or continuous fermentation conditions. Classical batch fermentation methods use a closed system, wherein the culture medium is made prior to the beginning of the fermentation run, the medium is inoculated with the desired organism(s), and fermentation occurs without the subsequent addition of any components to the medium. In certain cases, the pH and oxygen content, but not the carbon source content, of the growth medium are altered during batch methods. The metabolites and cell biomass of the batch system change constantly up to the time the fermentation is stopped. In a batch system, cells usually progress through a static lag phase to a high growth log phase and finally to a stationary phase where growth rate is diminished or halted. If untreated, cells in the stationary phase eventually die. In general terms, the cells in log phase produce most protein.

A variation on the standard batch system is the "fed-batch fermentation" system. In this system, nutrients (e.g., a carbon source, nitrogen source, $O_2$, and typically, other nutrients) are only added when their concentration in culture falls below a threshold. Fed-batch systems are useful when catabolite repression is apt to inhibit the metabolism of the cells and where it is desirable to have limited amounts of nutrients in the medium. Measurement of the actual nutrient concentration in fed-batch systems is estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined culture medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in some embodiments, a limiting nutrient such as the carbon source or nitrogen source is maintained at a fixed rate and all other parameters are allowed to moderate. In other systems, a number of factors affecting growth are altered continuously while the cell concentration, measured by media turbidity, is kept constant. Continuous systems strive to maintain steady state growth conditions. Thus, cell loss due to medium being drawn off may be balanced against the cell growth rate in the fermentation. Methods of modulating nutrients and growth factors for continuous fermentation processes as well as techniques for maximizing the rate of product formation are known to those of skill in the art and find use in the production of a protein of interest (e.g., a protease) according to the methods of the invention.

As indicated above, overexpression of ymaH in a host cell enhances the level of production of a protein of interest when compared to the level of production of the same protein in a corresponding wild-type or altered parent host cell. In some embodiments of the present invention, overexpression of ymaH in a *Bacillus* host cell results in an increase in the production of a protein of interest above the level obtained in the corresponding cell that does not overexpress ymaH. In some embodiments, the invention provides wild-type or recombinant (altered) *Bacillus* host cells that overexpress YmaH. In some embodiments the recombinant *Bacillus* host cell is a cell that was altered to produce greater levels of a protease than the unaltered parent/precursor *Bacillus* cell when grown under the same conditions.

The present invention also encompasses methods for producing a protein of interest in a modified cell that overexpresses ymaH in less time than that required by the precursor host cell. For example, the modified host cells of the invention are capable of producing a protein of interest at a greater level and at an earlier time than the corresponding unmodified precursor host cell. Thus, in some embodiments, the invention provides for methods of producing a protein of interest (e.g., a protease), at a level that is greater than that produced by the parent host cell and in about $\frac{1}{6}^{th}$ of the time it takes the precursor host cell to attain its maximum level of expression. In other embodiments, the modified host produces a protein of interest in about $\frac{1}{5}^{th}$, about $\frac{1}{4}^{th}$, about $\frac{1}{3}^{rd}$, or about $\frac{1}{2}$ of the time it takes the precursor host cell to attain its maximum level of expression.

Measurement of Production/Activity

In some embodiments, the invention provides for methods for enhancing the expression of a protein of interest from a *Bacillus* host cell by obtaining a modified *Bacillus* host that overexpresses ymaH, growing the modified *Bacillus* host under suitable growth conditions and allowing the host cell to produce the protein of interest at a level that is enhanced when compared to that of the precursor host cell. In some embodiments, the modified *Bacillus* cell is obtained from a wild-type *Bacillus* cell. In other embodiments, the modified *Bacillus* cell is obtained from an altered host cell. The level of production of a protein of interest by a host cell can be determined as a function of the activity of the produced protein. In some embodiments, the method for enhancing the expression of a protein of interest uses a modified *Bacillus* host cell that has been transformed with a polynucleotide construct that encodes YmaH and that is operably linked to a sigA and/or a sigH promoter. In some embodiments, the polynucleotide constructs comprise a sequence chosen from SEQ ID NOS: 1, 2, 3, and 13. In some embodiments, the polynucleotide construct is present on a plasmid that replicates in the *Bacillus* cell, while in other embodiments, the polynucleotide construct is integrated into the genome of the modified *Bacillus* cell. As discussed above, the modified *Bacillus* cell is capable of producing a protein of interest, including but not limited to that is chosen from amylolytic enzymes, proteolytic enzymes, cellulytic enzymes, oxidoreductase enzymes, and plant wall degrading enzymes. In further embodiments, these enzyme include but are not limited to amylases, proteases, xylanases, lipases, laccases, phenol oxidases, oxidases, cutinases, cellulases, hemicellulases, esterases, peroxidases, catalases, glucose oxidases, phytases, pectinases, glucosidases, isomerases, transferases, kinases phosphatases, galactosidases and chitinases. In other embodiments, the protein of interest is a hormone, cytokine, growth factor, receptor, vaccine, antibody, or the like. While it is not intended that the present invention be limited to any particular protein, in some particularly preferred embodiments, the protein of interest is a protease.

There are various assays known to those of ordinary skill in the art for detecting and measuring activity of proteins of interest produced by the host cells of the invention. In particular, assays are available for measuring protease activity that are based on the release of acid-soluble peptides from casein or hemoglobin, measured as absorbance at 405 nm or colorimetrically using the Folin method (See e.g., Bergmeyer et al., "Methods of Enzymatic Analysis" vol. 5, *Peptidases, Proteinases and their Inhibitors*, Verlag Chemie, Weinheim [1984]). Some other assays involve the solubilization of chromogenic substrates (See e.g., Ward, "Proteinases," in Fogarty (ed.)., *Microbial Enzymes and Biotechnology*, Applied Science, London, [1983], pp 251-317). Other exemplary assays include, but are not limited to succinyl-Ala-Ala-Pro-Phe-para nitroanilide assay (SAAPFpNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem., 223:119-129 [1994]; and Hsia et al., Anal Biochem., 242: 221-227 [1999]). It is not intended that the present invention be limited to any particular assay method(s).

Other means for determining the levels of production of a protein of interest in a host cell and detecting expressed proteins include the use of immunoassays with either polyclonal or monoclonal antibodies specific for the protein. Examples include enzyme-linked immunosorbent assay (ELISA), radioimmunoassay (RIA), fluorescence immunoassay (FIA), and fluorescent activated cell sorting (FACS). However, other methods are known to those in the art and find use in assessing the protein of interest (See e.g., Hampton et al., *Serological Methods, A Laboratory Manual*, APS Press, St. Paul, Minn. [1990]; and Maddox et al., J. Exp. Med., 158:1211 [1983]). In some preferred embodiments, production of a protein of interest is higher in the host cell of the present invention than in a corresponding wild-type or altered host. As known in the art, the *Bacillus* cells produced using the present invention are maintained and grown under conditions suitable for the expression and recovery of a polypeptide of interest from cell culture. It is not intended that the present invention be limited to any particular assay method(s).

One measure of enhancement of the level of production of a protease by a modified host cell of the invention above the level of production of the same protease by a wild-type or altered parent host cell can be determined as an activity ratio. The activity ratio can be expressed as the ratio of the enzymatic activity of the protein of interest produced by a host cell that overexpresses ymaH to the enzymatic activity of the protein of interest produced by the corresponding host cell that does not overexpress ymaH. A ratio equal or greater than 1 indicates that the protein of interest produced by the host cell that overexpresses YmaH is produced at levels equal or greater than those at which the same protein of interest is produced by the corresponding host cell that does not overexpress ymaH. For example, an activity ratio of 1.5 indicates that the protein of interest is produced by the host cell that overexpresses ymaH at 1.5 times the level at which the same protein of interest is produced by a corresponding host cell that does not overexpress ymaH when grown under the same conditions (i.e. host cells that overexpress ymaH produce 50% more protein of interest than the corresponding host cell that does not overexpress ymaH). In some embodiments, the activity ratio is at least 1, at least about 1.05, about at least about 1.1, at least about 1.2, at least about 1.3, at least about 1.4, at least about 1.5, at least about 1.6, at least about 1.7, at least about 1.8. at least about 1.9, or at least about 2. In other embodiments, the activity ratio is at least about 2.1, at least about 2.2, at least about 2.3, at least about 2.4, at least about 2.5, at least about 2.6, at least about 2.7, at least about 2.8, at least about 2.9, or at least about 3. In yet other embodiments, the activity ratio is at least about 3.5, at least about 4.0, or at least about 5. In some embodiments, a ratio of 1 or greater is desired.

Alternatively, the level of production of a protease by a modified host cell of the invention can be related as a percent increase above the level of production of the parent host cell. In the methods of the present invention, the modified *Bacillus* cell preferably produces at least about 25% more, more preferably at least about 50% more, more preferably at least about 75% more, more preferably at least about 100% more, even more preferably at least about 200% more, most preferably at least about 300% more, and even most preferably at least about 400% more polypeptide relative to a wild-type or altered parent host. Thus, in some embodiments, production of a protein of interest by a host cell that overexpresses ymaH is enhanced by at least about 0.5%, about 1.0%, about 1.5%, about 2.0%, about 2.5%, about 3.0%, about 4.0%, about 5.0%, about 8.0%, about 10%, about 15%, about 20%, about 25%, about 30%, about 40%, about 50%, at least about 60%, at least about 70%, at least about 80%, at least about 90%, at least about 100% or more, compared to the production of the same protein of interest by a host cell that does not overexpress ymaH. In other embodiments, production of a protein of interest by a host cell that overexpresses ymaH is enhanced by at least about 110%, about 120%, about 130%, about 140%, about 150%, about 160%, about 170%, about 180%, about 190%, and up to at least about 200%, or more compared to the production of the same protein of interest by a host cell that does not overexpress ymaH.

In order to further illustrate the present invention and advantages thereof, the following specific Examples are given with the understanding that they are being offered to illustrate the present invention and should not be construed in any way as limiting its scope.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ppm (parts per million); M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); °C. (degrees Centigrade); QS (quantity sufficient); ND (not done); NA (not applicable); rpm (revolutions per minute); H$_2$O (water); dH$_2$O (deionized water); (HCl (hydrochloric acid); aa (amino acid); by (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); MgCl$_2$ (magnesium chloride); NaCl (sodium chloride); Cm (chloramphenicol); w/v (weight to volume); v/v (volume to volume); g (gravity); OD (optical density); Dulbecco's phosphate buffered solution (DPBS); OD$_{280}$ (optical density at 280 nm); OD$_{600}$ (optical density at 600 nm); A$_{405}$ (absorbance at 405 nm); PAGE (polyacrylamide gel electrophoresis); PBS (phosphate buffered saline [150 mM NaCl, 10 mM sodium phosphate buffer, pH 7.2]); PBST (PBS+0.25% TWEEN®-20); PEG (polyethylene glycol); PCR (polymerase chain reaction); SDS (sodium dodecyl sulfate); Tris (tris(hydroxymethyl)aminomethane); HEPES (N-[2-Hydroxyethyl]piperazine-N-[2-ethanesulfonic acid]); HBS (HEPES buffered saline); SDS (sodium dodecylsulfate); bME, BME and βME (beta-mercaptoethanol or 2-mercaptoethanol); Tris-HCl (tris[Hydroxymethyl]aminomethane-hydrochloride); Tricine (N-[tris-(hydroxymethyl)-methyl]-glycine); DMSO (dimethyl sulfoxide); Taq (*Thermus aquaticus* DNA polymerase); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetracetic acid); bla (β-lactamase or ampicillin-resistance gene); DNA2.0 (DNA2.0, Menlo Park, Calif.); OXOID (Oxoid, Basingstoke, Hampshire, UK); Corning (Corning Life Sciences, Corning, N.Y.); ATCC (American Type Culture Collection, Rockville, Md.); Sequetech (Sequetech Corporation, Mountainview, Calif.); Gibco/BRL (Gibco/BRL, Grand Island, N.Y.); Sigma (Sigma Chemical Co., St. Louis, Mo.); Pharmacia (Pharmacia Biotech, Pisacataway, N.J.); NCBI (National Center for Biotechnology Information); Applied Biosystems (Applied Biosystems, Foster City, Calif.); Clontech (CLONTECH Laboratories, Palo Alto, Calif.); Operon Technologies (Operon Technologies, Inc., Alameda, Calif.); Bachem (Bachem Bioscience, Inc., King of Prussia, Pa.); Difco (Difco Laboratories, Detroit, Mich.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); and Microsoft (Microsoft, Inc., Redmond, Wash.).

Example 1

Generation of SigA and SigH Polynucleotide Constructs

Polynucleotide constructs SigH, SigA1 and SigA2 were generated to overexpress ymaH in host cells of *B. subtilis*.

PCR primers were designed to be homologous to the *Bacillus subtilis* genome (FIG. 1A) and to contain a 6 base pair restriction enzyme site located 6 base pairs from the 5' end of the primer. Primers were designed to engineer unique restriction sites at the upstream and downstream ends of the construct. The primary source of genome sequence (Kunst et al., Nature 390:249-256 [1997]), gene localization, and start and stop codon information was obtained from the NCBI Database: Completed *Bacillus subtilis* subsp. *subtilis* str. 168, or from the SubtiList World Wide Web Server known to those in the art (Moser, I. 1998. FEBS Lett. 430(1-2):28-36). The sequence considered is reported as SEQ ID NO:13 with coordinates 1865428-18670191 in the NCBI database, ACC No NC000964.

The SigH construct (SEQ ID NO:1) was generated to comprise the polynucleotide sequence encompassing the Sigma H promoter and the adjacent sequence encoding the YmaH protein. The Sigma H promoter is naturally located within the polynucleotide sequence encoding the miaA gene, close to the 3' end of the gene, and immediately upstream of the ymaH gene. The entire Sigma H promoter and adjacent ymaH coding sequence was amplified by PCR using the forward primer P1: GGCACCGAATTCGACGTGGTTTCGCAA-CAAAATGCAG (SEQ ID NO:5; position 987 to 1011 of SEQ ID NO:13), with an EcoRI restriction site added at the 5' end, and a reverse primer P2: GGCACCGGATCCCTCAT-AAAAAAAGACCGTGCCTTGG (SEQ ID NO:6, at position 1472 to 1496 of SEQ ID NO:13), with and added BamHI restriction site (FIG. 1 B).

The SigA1 and SigA2 constructs were generated in a three step process by 1) amplifying individual fragments of *B. subtilis* chromosomal DNA, 2) purifying and assembling the fragments; and 3) amplifying the assembled product by PCR. The SigA1 construct (SEQ ID NO:2) was generated using two sets of primers (FIG. 1C). A first set of primers: forward primer P3: GCGCCGAATTCTCATACCCTGAAAG-GAAAGACAAGG (SEQ ID NO: 7) located at the 5' end of SEQ ID NO: 13; and reverse primer P4: TTCGAGTTTTC-CTGCTATATGTGTGGGGCTGCTTCGTAT-TATTCAATATG (SEQ ID NO:8) located from by 153 to by 177 on the SEQ ID NO:13, was used to amplify a first fragment containing the SigA promoter, Ribosome Binding Site, start codon and the first few codons of the miaA gene. A second set of primers, forward primer P5: CATAT-TGAATAATACGAAGCAGCCCCACA-CATATAGCAGGAAAACTCGAA (SEQ ID NO:9) located from by 1071 to by 1095 on the SEQ ID NO: 13 and reverse primer P2 (SEQ ID NO:6), were used to amplify a second fragment containing the DNA sequence encoding the YmaH protein. Reverse primer P4 and forward primer P5 are fusion primers that were designed to contain tails that are complementary to each other but that are not homologous to the sequence that is being amplified to eliminate the intervening miaA coding sequence. The two fragments were annealed, and the resulting SigA1 construct contained the SigA promoter, the ribosome binding site and the transcription start site of the miaA gene. The SigA1 construct was amplified using forward primer P3 (SEQ ID NO:7) and reverse primer P2 (SEQ ID NO:6), which respectively contain an EcoRI and a BamHI restriction site, and ligated into the polylinker of replicating plasmid pBS19. The polynucleotide sequence of pBS19 is shown below (SEQ ID NO:12). The pBS19 plasmid can replicate in *E. coli* and *B. subtilis*, and carries the chloramphenicol resistance selection marker gene.

(SEQ ID NO: 12)
GAATTCGAGCTCGGTACCCGGGGATCCTCTAGAGTCGACCTGCAGGCATG

CAAGCTTGGCGATCCTGCCTCGCGCGTTTCGGTGATGACGGTGAAAACCT

CTGACACATGCAGCTCCCGGAGACGGTCACAGCTTGTCTGTAAGCGGATG

CCGGGAGCAGACAAGCCCGTCAGGGCGCGTCAGCGGGTGTTGGCGGGTGT

CGGGGCGCAGCCATGACCCAGTCACGTAGCGATAGCGGAGTGTATACTGG

CTTAACTATGCGGCATCAGAGCAGATTGTACTGAGAGTGCACCATATGCG

GTGTGAAATACCGCACAGATGCGTAAGGAGAAAATACCGCATCAGGCGCT

CTTCCGCTTCCTCGCTCACTGACTCGCTGCGCTCGGTCGTTCGGCTGCGG

CGAGCGGTATCAGCTCACTCAAAGGCGGTAATACGGTTATCCACAGAATC

AGGGGATAACGCAGGAAAGAACATGTGAGCAAAAGGCCAGCAAAAGGCCA

GGAACCGTAAAAAGGCCGCGTTGCTGGCGTTTTTCCATAGGCTCCGCCCC

CCTGACGAGCATCACAAAAATCGACGCTCAAGTCAGAGGTGGCGAAACCC

GACAGGACTATAAAGATACCAGGCGTTTCCCCCTGGAAGCTCCCTCGTGC

GCTCTCCTGTTCCGACCCTGCCGCTTACCGGATACCTGTCCGCCTTTCTC

CCTTCGGGAAGCGTGGCGCTTTCTCATAGCTCACGCTGTAGGTATCTCAG

TTCGGTGTAGGTCGTTCGCTCCAAGCTGGGCTGTGTGCACGAACCCCCCG

TTCAGCCCGACCGCTGCGCCTTATCCGGTAACTATCGTCTTGAGTCCAAC

CCGGTAAGACACGACTTATCGCCACTGGCAGCAGCCACTGGTAACAGGAT

TAGCAGAGCGAGGTATGTAGGCGGTGCTACAGAGTTCTTGAAGTGGTGGC

CTAACTACGGCTACACTAGAAGGACAGTATTTGGTATCTGCGCTCTGCTG

AAGCCAGTTACCTTCGGAAAAAGAGTTGGTAGCTCTTGATCCGGCAAACA

AACCACCGCTGGTAGCGGTGGTTTTTTTGTTTGCAAGCAGCAGATTACGC

GCAGAAAAAAAGGATCTCAAGAAGATCCTTTGATCTTTTCTACGGGGTCT

GACGCTCAGTGGAACGAAAACTCACGTTAAGGGATTTTGGTCATGAGATT

ATCAAAAAGGATCTGGAGCTGTAATATAAAAACCTTCTTCAACTAACGGG

GCAGGTTAGTGACATTAGAAAACCGACTGTAAAAAGTACAGTCGGCATTA

TCTCATATTATAAAAGCCAGTCATTAGGCCTATCTGACAATTCCTGAATA

GAGTTCATAAACAATCCTGCATGATAACCATCACAAACAGAATGATGTAC

CTGTAAAGATAGCGGTAAATATATTGAATTACCTTTATTAATGAATTTTC

CTGCTGTAATAATGGGTAGAAGGTAATTACTATTATTATTGATATTTAAG

TTAAACCCAGTAAATGAAGTCCATGGAATAATAGAAAGAGAAAAAGCATT

TTCAGGTATAGGTGTTTTGGGAAACAATTTCCCCGAACCATTATATTTCT

CTACATCAGAAAGGTATAAATCATAAAACTCTTTGAAGTCATTCTTTACA

GGAGTCCAAATACCAGAGAATGTTTTAGATACACCATCAAAAATTGTATA

AAGTGGCTCTAACTTATCCCAATAACCTAACTCTCCGTCGCTATTGTAAC

CAGTTCTAAAAGCTGTATTTGAGTTTATCACCCTTGTCACTAAGAAAATA

AATGCAGGGTAAAATTTATATCCTTCTTGTTTTATGTTTCGGTATAAAAC

ACTAATATCAATTTCTGTGGTTATACTAAAAGTCGTTTGTTGGTTCAAAT

AATGATTAAATATCTCTTTTCTCTTCCAATTGTCTAAATCAATTTTATTA

AAGTTCATTTGATATGCCTCCTAAATTTTTATCTAAAGTGAATTTAGGAG

GCTTACTTGTCTGCTTTCTTCATTAGAATCAATCCTTTTTTAAAAGTCAA

TATTACTGTAACATAAATATATATTTTAAAAATATCCCACTTTATCCAAT

TTTCGTTTGTTGAACTAATGGGTGCTTTAGTTGAAGAATAAAAGACCACA

TTAAAAAATGTGGTCTTTTGTGTTTTTTTAAAGGATTTGAGCGTAGCGAA

```
AAATCCTTTTCTTTCTTATCTTGATAATAAGGGTAACTATTGCCGGTTGT
CCATTCATGGCTGAACTCTGCTTCCTCTGTTGACATGACACACATCATCT
CAATATCCGAATAGGGCCCATCAGTCTGACGACCAAGAGAGCCATAAACA
CCAATAGCCTTAACATCATCCCCATATTTATCCAATATTCGTTCCTTAAT
TTCATGAACAATCTTCATTCTTTCTTCTCTAGTCATTATTATTGGTCCAT
TCACTATTCTCATTCCCTTTTCAGATAATTTTAGATTTGCTTTTCTAAAT
AAGAATATTTGGAGAGCACCGTTCTTATTCAGCTATTAATAACTCGTCTT
CCTAAGCATCCTTCAATCCTTTTAATAACAATTATAGCATCTAATCTTCA
ACAAACTGGCCCGTTTGTTGAACTACTCTTTAATAAAATAATTTTTCCGT
TCCCAATTCCACATTGCAATAATAGAAAATCCATCTTCATCGGCTTTTTC
GTCATCATCTGTATGAATCAAATCGCCTTCTTCTGTGTCATCAAGGTTTA
ATTTTTTATGTATTTCTTTTAACAAACCACCATAGGAGATTAACCTTTTA
CGGTGTAAACCTTCCTCCAAATCAGACAAACGAGGATATTTTGCAGTTTC
GTCAATTGCCGATTGTATATCCGATTTATATTTATTTTTCGGTCGAATCA
TTTGAACTTTTACATTTGGATCATAGTCTAATTTCATTGCCTTTTTCCAA
AATTGAATCCATTGTTTTTGATTCACGTAGTTTTCTGTATTCTTAAAATA
AGTTGGTTCCACACATACCAATACATGCATGTGCTGATTATAAGAATTAT
CTTTATTATTTATTGTCACTTCCGTTGCACGCATAAAACCAACAAGATTT
TTATTAATTTTTTTATATTGCATCATTCGGCGAAATCCTTGAGCCATATC
TGACAAACTCTTATTTAATTCTTCGCCATCATAAACATTTTTAACTGTTA
ATGTGAGAAACAACCAACGAACTGTTGGCTTTTGTTTAATAACTTCAGCA
ACAACCTTTTGTGACTGAATGCCATGTTTCATTGCTCTCCTCCAGTTGCA
CATTGGACAAAGCCTGGATTTACAAAACCACACTCGATACAACTTTCTTT
CGCCTGTTTCACGATTTTGTTTATACTCTAATATTTCAGCACAATCTTTT
ACTCTTTCAGCCTTTTTAAATTCAAGAATATGCAGAAGTTCAAAGTAATC
AACATTAGCGATTTTCTTTTCTCTCCATGGTCTCACTTTTCCACTTTTTG
TCTTGTCCACTAAAACCCTTGATTTTTCATCTGAATAAATGCTACTATTA
GGACACATAATATTAAAAGAAACCCCCATCTATTTAGTTATTTGTTTAGT
CACTTATAACTTTAACAGATGGGGTTTTTCTGTGCAACCAATTTTAAGGG
TTTTCAATACTTTAAAACACATACATACCAACACTTCAACGCACCTTTCA
GCAACTAAAATAAAAATGACGTTATTTCTATATGTATCAAGATAAGAAAG
AACAAGTTCAAAACCATCAAAAAAAGACACCTTTTCAGGTGCTTTTTTA
TTTTATAAACTCATTCCCTGATCTCGACTTCGTTCTTTTTTTACCTCTCG
GTTATGAGTTAGTTCAAATTCGTTCTTTTTAGGTTCTAAATCGTGTTTTT
CTTGGAATTGTGCTGTTTTATCCTTTACCTTGTCTACAAACCCCTTAAAA
ACGTTTTTAAAGGCTTTTAAGCCGTCTGTACGTTCCTTAAG
```

The SigA2 construct (SEQ ID NO:3) was generated according to the method described for the construction of the SigA1 construct using the following primers (FIG. 1D). The first fragment containing the SigA promoter was amplified using forward primer P3 (SEQ ID NO:7) and reverse fusion primer P7: CATACAGTTTCGATTAAAGTTCGAG-CACTCTCTTTTATAAATCTCCCCCA (SEQ ID NO:11) located from by 125 to by 149 on the SEQ ID NO:13. The second fragment containing the DNA sequence encoding the YmaH protein was amplified using the forward fusion primer P6: TG GGGGAGATTTATAAAAGAGAGTGCTC-GAACTTTAATCGAAACTGTATG (SEQ ID NO:10) located from by 1090 to by 1114 on the SEQ ID NO:13 and the reverse primer P2 (SEQ ID NO:6). The two fragments were annealed, and the resulting SigA2 construct contained the SigA promoter, the ribosome binding site and the transcription start site of the ymaH gene.

The invention also encompasses a fourth SigA construct (SigA3; SEQ ID NO: 13; FIG. 1E), which is generated by amplifying the miaA ymaH region of the *Bacillus* chromosomal DNA that includes a SigA promoter, the region encoding the MiaA protein, the SigH YmaH promoter and the region encoding the YmaH protein.

The SigA3 construct was generated using forward primer GCGCGCGAATTCAGGGAAATTGTCG-GCAATGAGCCGCTCGGC (SEQ ID NO:18) and reverse primer GCGCGCCATGGCTGATTCGTCTCAGT-TCTGCTTCACTTTCA (SEQ ID NO: 19). SEQ ID NO:13 places an EcoRI restriction site at the 5' end of the fragment, while SEQ ID NO:19 places a NcoI site at the other end. This allows to clone the fragment in the pBN3 vector reported as SEQ ID NO:20, shown below.

```
                                            (SEQ ID NO: 20)
GACGTCTAAGAAACCATTATTATCATGACATTAACCTATAAAAATAGGCG
TATCACGAGGCCCTTTCGTCTTCAAGAATTAATTCTCATGTTTGACAGCT
TATCATCGATAAGCTTGCATGCCTGCAGGTCGACTCTAGAGGATCCCCGG
GTACCGAGCTCGAATTCCTTAAGGAACGTACAGACGGCTTAAAAGCCTTT
AAAAACGTTTTTAAGGGGTTTGTAGACAAGGTAAAGGATAAAACAGCACA
ATTCCAAGAAAAACACGATTTAGAACCTAAAAAGAACGAATTTGAACTAA
CTCATAACCGAGAGGTAAAAAAAGAACGAAGTCGAGATCAGGGAATGAGT
TTATAAAATAAAAAAAGCACCTGAAAAGGTGTCTTTTTTTGATGGTTTTG
AACTTGTTCTTTCTTATCTTGATACATATAGAAATAACGTCATTTTTATT
TTAGTTGCTGAAAGGTGCGTTGAAGTGTTGGTATGTATGTGTTTTAAAGT
ATTGAAAACCCTTAAAATTGGTTGCACAGAAAAACCCCATCTGTTAAAGT
TATAAGTGACTAAACAAATAACTAAATAGATGGGGGTTTCTTTTAATATT
ATGTGTCCTAATAGTAGCATTTATTCAGATGAAAAATCAAGGGTTTTAGT
GGACAAGACAAAAAGTGGAAAAGTGAGACCATGGAGAGAAAAGAAAATCG
CTAATGTTGATTACTTTGAACTTCTGCATATTCTTGAATTTAAAAAGGCT
GAAAGAGTAAAAGATTGTGCTGAAATATTAGAGTATAAACAAAATCGTGA
AACAGGCGAAAGAAAGTTGTATCGAGTGTGGTTTTGTAAATCCAGGCTTT
GTCCAATGTGCAACTGGAGGAGAGCAATGAAACATGGCATTCAGTCACAA
AAGGTTGTTGCTGAAGTTATTAAACAAAAGCCAACAGTTCGTTGGTTGTT
TCTCACATTAACAGTTAAAAATGTTTATGATGGCGAAGAATTAAATAAGA
GTTTGTCAGATATGGCTCAAGGATTTCGCCGAATGATGCAATATAAAAAA
ATTAATAAAAATCTTGTTGGTTTTATGCGTGCAACGGAAGTGACAATAAA
TAATAAAGATAATTCTTATAATCAGCACATGCATGTATTGGTATGTGTGG
AACCAACTTATTTTAAGAATACAGAAAACTACGTGAATCAAAAACAATGG
ATTCAATTTTGGAAAAAGGCAATGAAATTAGACTATGATCCAAATGTAAA
```

```
AGTTCAAATGATTCGACCGAAAAATAAATATAAATCGGATATACAATCGG
CAATTGACGAAACTGCAAAATATCCTGTAAAGGATACGGATTTTATGACC
GATGATGAAGAAAAGAATTTGAAACGTTTGTCTGATTTGGAGGAAGGTTT
ACACCGTAAAAGGTTAATCTCCTATGGTGGTTTGTTAAAAGAAATACATA
AAAAATTAAACCTTGATGACACAGAAGAAGGCGATTTGATTCATACAGAT
GATGACGAAAAAGCCGATGAAGATGGATTTTCTATTATTGCAATGTGGAA
TTGGGAACGGAAAAATTATTTTATTAAAGAGTAGTTCAACAAACGGGCCA
GTTTGTTGAAGATTAGATGCTATAATTGTTATTAAAAGGATTGAAGGATG
CTTAGGAAGACGAGTTATTAATAGCTGAATAAGAACGGTGCTCTCCAAAT
ATTCTTATTTAGAAAAGCAAATCTAAAATTATCTGAAAAGGGAATGAGAA
TAGTGAATGGACCAATAATAATGACTAGAGAAGAAAGAATGAAGATTGTT
CATGAAATTAAGGAACGAATATTGGATAAATATGGGGATGATGTTAAGGC
TATTGGTGTTTATGGCTCTCTTGGTCGTCAGACTGATGGGCCCTATTCGG
ATATTGAGATGATGTGTGTCATGTCAACAGAGGAAGCAGAGTTCAGCCAT
GAATGGACAACCGGTGAGTGGAAGGTGGAAGTGAATTTTGATAGCGAAGA
GATTCTACTAGATTATGCATCTCAGGTGGAATCAGATTGGCCGCTTACAC
ATGGTCAATTTTCTCTATTTTGCCGATTTATGATTCAGGTGGATACTTA
GAGAAAGTGTATCAAACTGCTAAATCGGTAGAAGCCCAAACGTTCCACGA
TGCGATTTGTGCCCTTATCGTAGAAGAGCTGTTTGAATATGCAGGCAAAT
GGCGTAATATTCGTGTGCAAGGACCGACAACATTTCTACCATCCTTGACT
GTACAGGTAGCAATGGCAGGTGCCATGTTGATTGGTCTGCATCATCGCAT
CTGTTATACGACGAGCGCTTCGGTCTTAACTGAAGCAGTTAAGCAATCAG
ATCTTCCTTCAGGTTATGACCATCTGTGCCAGTTCGTAATGTCTGGTCAA
CTTTCCGACTCTGAGAAACTTCTGGAATCGCTAGAGAATTTCTGGAATGG
GATTCAGGAGTGGACAGAACGACACGGATATATAGTGGATGTGTCAAAAC
GCATACCATTTTGAACGATGACCTCTAATAATTGTTAATCATGTTGGTTA
CCTGCCTCGCGCGTTTCGGTGATGACGGTGAAAACCTCTGACACATGCAG
CTCCCGGAGACGGTCACAGCTTGTCTGTAAGCGGATGCCGGGAGCAGACA
AGCCCGTCAGGGCGCGTCAGCGGGTGTTGGCGGGTGTCGGGCGCAGCCA
TGACCCAGTCACGTAGCGATAGCGGAGTGTATACTGGCTTAACTATGCGG
CATCAGAGCAGATTGTACTGAGAGTGCACCATATGCGGTGTGAAATACCG
CACAGATGCGTAAGGAGAAAATACCGCATCAGGCGCTCTTCCGCTTCCTC
GCTCACTGACTCGCTGCGCTCGGTCGTTCGGCTGCGGCGAGCGGTATCAG
CTCACTCAAAGGCGGTAATACGGTTATCCACAGAATCAGGGGATAACGCA
GGAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCC
GACCCTGCCGCTTACCGGATACCTGTCCGCCTTTCTCCCTTCGGGAAGCG
TGGCGCTTTCTCATAGCTCACGCTGTAGGTATCTCAGTTCGGTGTAGGTC
GTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACG
ACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTA
CACTAGAAGGACAGTATTTGGTATCTGCGCTCTGCTGAAGCCAGTTACCT
TCGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAGG
ATCTCAAGAAGATCCTTTGATCTTTTCTACGGGGTCTGACGCTCAGTGGA
ACGAAAACTCACGTTAAGGGATTTTGGTCATGAGATTATCAAAAGGATC
TTCACCTAGATCCTTTTAAATTAAAAATGAAGTTTTAAATCAATCTAAAG
TATATATGAGTAAACTTGGTCTGACAGTTACCAATGCTTAATCAGTGAGG
CACCTATCTCAGCGATCTGTCTATTTCGTTCATCCATAGTTGCCTGACTC
CCCGTCGTGTAGATAACTACGATACGGGAGGGCTTACCATCTGGCCCCAG
TGCTGCAATGATACCGCGAGACCCACGCTCACCGGCTCCAGATTTATCAG
CAATAAACCAGCCAGCCGGAAGGGCCGAGCGCAGAAGTGGTCCTGCAACT
TTATCCGCCTCCATCCAGTCTATTAATTGTTGCCGGGAAGCTAGAGTAAG
TAGTTCGCCAGTTAATAGTTTGCGCAACGTTGTTGCCATTGCTACAGGCA
TCGTGGTGTCACGCTCGTCGTTTGGTATGGCTTCATTCAGCTCCGGTTCC
CAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGT
TATCACTCATGGTTATGGCAGCACTGCATAATTCTCTTACTGTCATGCCA
TCCGTAAGATGCTTTTCTGTGACTGGTGAGTACTCAACCAAGTCATTCTG
AGAATAGTGTATGCGGCGACCGAGTTGCTCTTGCCCGGCGTCAATACGGG
ATAATACCGCGCCACATAGCAGAACTTTAAAAGTGCTCATCATTGGAAAA
CGTTCTTCGGGGCGAAAACTCTCAAGGATCTTACCGCTGTTGAGATCCAG
TTCGATGTAACCCACTCGTGCACCCAACTGATCTTCAGCATCTTTTACTT
TCACCAGCGTTTCTGGGTGAGCAAAAACAGGAAGGCAAAATGCCGCAAAA
AAGGGAATAAGGGCGACACGGAAATGTTAATACTCATACTCTTCCTTTT
TCAATATTATTGAAGCATTTATCAGGGTTATTGTCTCATGAGCGGATACA
TATTTGAATGTATTTAGAAAAATAAACAAATAGGGGTTCCGCGCACATTT
CCCCGAAAAGTGCCACCT
```

All PCR reactions were performed in 50 μl volume containing 1-2 ul DNA or from a colony resuspension, 5 μl of 10×Pfu Ultra buffer (Stratagene), 1 uL of 10 mM dNTP blend (Roche), 0.5 uL of 0.2 uM primers, 1 μl Pfu Ultra High Fidelity Polymerase, and the volume adjusted with water to have a total volume of 50μ. The PCR conditions were: 95 C for 2 min, 30 cycles of 95 C for 30 sec, 62 C for 30 sec, 72 C for 1 min, followed by 1 cycle of 72 C for 10 min.

The obtained PCR fragments were gel purified using Qiagen Gel Purification Kit according to the manufacturer's instructions.

Fusion constructs were obtained by annealing 0.25 ul aliquots of purified PCR fragments that were mixed together and added into fresh PCR mix following the above recipe using primers P3 and P2. The total volume of the PCR mixture was 50 μl. The PCR conditions were the same as above adjusting the annealing temperature according to the Tm of the primers.

The desired SigH, SigA1, and SigA2 constructs were ligated into pBS19 plasmids that had been digested with EcoRI and BamHI to generate SigA and SigH expression vectors that were used to transform host cells as described in Example 2.

The transformation mixture was plated on LB+1.6% skim milk+5 ug/ml cmp plates. Next day, halo-forming colonies were picked and plated for single colonies. The colony purification was performed twice. Five individual clones were analyzed by sequencing of aprE promoter region. All of them had consensus sequence at −35 region of aprE promoter.

Example 2

Host Cell Transformation and Expression of aprE Protease

Five microliters of the ligation mixture containing the SigA or SigH constructs were used to transform *E. coli* Top10 cells (Invitrogen) by electroporation. The transformed cells were plated onto LB agar plates containing 5 ppm/ml chloramphenicol (Cm), and colonies were allowed to grow overnight at 37 C. Individual colonies were picked and transferred to tubes containing 5 ml of LB+5 ppm/ml Cm. Cultures were grown overnight at 37° C. while shaking at 250 rpm. Plasmid DNA was prepared from the *E. coli* cultures, and a portion of the plasmid DNA preparation was sequenced (Sequetech). Automated sequence analysis was performed using Phrep, Phrap, Consed, Custal W software.

The plasmid bearing the right construct from each of the three expression vectors was used to transform *B. subtilis* host cells. The expression vectors containing the SigH (SEQ ID NO:1) and SigA1 (SEQ ID NO:2) and SigA2 (SEQ ID NO:3) constructs were named pBS19 ymaH-H and pBS19 ymaH-A1 and pBS19 ymaH-A2 were transformed into *B. subtilis* strains BG2941 and BG2942 as follows. Two microliters of the plasmid DNA carrying the appropriate constructs were used to transform 100 µl of *B. substilis* cells BG 2941 (ΔnprE, amyE::PxylRA-comK-phleoR) and BG2942 (ΔnprE, degU (Hy)32, amyE::PxylRA-comK-phleoR). The BG2941 and BG2942 transformants carrying the SigH constructs were named 41SigH and 42SigH, respectively; and the BG2941 and BG2942 transformants carrying the SigA1 constructs were named 41SigA1 and 42SigA1, respectively. Some BG2941 and BG2942 host cells were also transformed with a control pBS19 plasmid, and were named 41pBS19 and 42pBS19. Both BG 2941 and BG2942 host cells carry the deletion of the nprE gene, which abolishes most of the non-aprE background proteolytic activity, thus facilitating the measurement of the alkaline protease (aprE) produced. The BG2941 and 2942 host cells also carry the cassette amyE::PxylRA-comK-phleoR, which allows to make competent cells by inducing a growing culture with xylose (Hahn et al., Mol Microbiol. 18:755-67 [1995]). The 2942 host cells also carry a mutation in the degU gene (degU(Hy)32 mutation), which alone increases the level of subtilisin secreted by the host cells by several fold relative to that secreted by host cells that do not carry the degU(Hy) mutation (Msadek et al. J Bacteriol, 172:824-834 [1990])

The effect of overexpressing YmaH in *Bacillus* host cells was determined qualitatively and quantitatively in assays described in Example 3.

Example 3

Effect of Overexpressing ymaH on the Production of Protease

Casein assay:—The effect of overexpressing ymaH on the production of protease by *Bacillus* host cells was determined first by a qualitative assay that compares the size of the halos produced by the colonies grown on agar plates containing casein in the form of skim milk. As protease enzyme is secreted by the *Bacillus* cells, it digests the casein in the skim milk, and forms regions of clearing, or halos around the growing colony. Host cells which have an inactive protease will exhibit little or no halo around the colonies. Thus, the size of the halo provides a qualitative assessment of the amount of protease that is produced by the secreting colony (Wells, T. A. et al. Nucleic Acids Res., 11, 7911-7925: [1983]).

BG2941 and BG2942 *B. subtilis* host cells transformed with SigH or SigA1 expression vectors were plated onto LB agar plates containing 1.6% skim milk and 5 ppm Cm/ml, and incubated overnight in at 37° C. The following day, colonies from some of the transformants were single colony isolated on LB agar plates with 5 ppm/ml Cm, and the plates were incubated overnight at 37 C. Single colony isolates were picked and patched on the same type of plates and incubated again at 37° C. overnight.

The largest halos were produced by the 42SigH host cells, which carry the degU(Hy)32 mutation and the SigH construct that enables the overexpression of ymaH. In particular, the size of the halos of the 42SigH cells evidences that overexpressing ymaH further enhances the production of subtilisin in host cells that already produce levels of the enzyme that are greater than those produced by wild-type cells i.e. 42SigH cells produce halos that are bigger than those produced by the 42pBS19 cells, which carry the degU(Hy) mutation but do not carry a construct that enables overexpression of ymaH, but which in turn produce halos that are bigger than the halos produced by the 41pBS19 cells, which do not carry the degU (Hy)32 mutation and do not carry a construct that enables overexpression of ymaH. The halos produced by the 42SigH cells were also greater than the halos produced by the 41 SigH cells, which do not carry the degU(Hy) mutation but carry the SigH construct to enable overexpression of ymaH.

AAPF assay—The production of subtilisin by transformed *Bacillus* host cells 42SigH, 42SigA1, 41SigA2, which overexpress ymaH, and their respective controls 42pBS19, and 41pBS19 was quantified as a function of the activity of the secreted aprE protease. The proteolytic activity of the secreted protease was determined as the rate of hydrolysis of the substrate succinyl-L-Ala-L-Ala-L-Pro-L-Phe-p-nitroanalide (AAPF from Sigma Chemical Co). The assay measured the level of production of protease as the absorbance at 405 nm/min resulting from the hydrolysis and release of p-nitroanaline (Estell et al., J Biol Chem., 260:6518-6521 [1985]). The measurements were made using the Sofmax Pro software, and the specified conditions were set as: Type: Kinetic; Reduction: Vmax Points (Read best $^{15}/_{28}$ points); Lm1: 405 nm; Time: 5 minutes; and Interval: 11 Seconds.

Liquid cultures of *B. subtilis* control host cells 41pBS19 and 42pBS19, and host cells overexpressing ymaH were obtained by inoculating 5 ml of LB containing 5 pmm/ml of chloramphenicol (Cm) with single colonies of transformed cells 41SigH and 42SigA1 and 42SigH, and allowing the cells to grow while shaking at 37 C until growth reached mid-logarithmic phase. Each of the cultures was diluted 1:100 with fresh complex medium containing 5 ppm/ml Cm, and allowed to grow at 37° C. while shaking at 250 rpm. Samples of the cultures were taken at the times indicated in the figures. The samples were centrifuged and the supernatants were tested for production of subtilisin.

Ten microliters of each of the *B. subtilis* cultures supernatants were diluted 100 ul of Tris Buffer, containing 10 mM Tris+0.005% TWEEN®-80, pH 8.6; and 25 ul of 100 mg/ml AAPF. The activity of each of the protease was calculated, and the effect of overexpressing YmaH on the production of the protease is shown in FIGS. 3A-B and FIG. 4.

FIGS. 3A and 3B show that overexpressing ymaH in *Bacillus* host cells, whether in presence (42SigA and 42SigH; FIG. 3A) or absence (41 SigH; FIG. 3B) of the degU(Hy) mutation, enhances the production of the aprE subtilisin by several fold when compared to the level produces by the respective control cells 41pBS19 and 42pBS19. In addition, cells that overexpress yamH produce elevated levels of subtilisin earlier than cells that do not overexpress ymaH. For example, FIG. 3A shows that 42sigH cells produce almost as much subtilisin at 20 hours of growth as the parent control cells produce at 48 hours. Similarly, FIG. 3B shows that 41 SigH cells produce more subtilisin at 25 hours than the 41 pBS control cells produce at 48 hours. The graph shown in FIG. 4 shows that cells that the expression of ymaH when driven by the SigH promoter (42SigH) results in the production of subtilisin that is greater than that produced by cells in which ymaH expression is driven by the sigma promoter (42SigA). FIG. 4 also shows that overexpression of ymaH whether driven by the SigH or SigA promoter results in enhanced production of subtilisin as early as after only one hour of cell growth.

We claim:

1. An isolated chimeric polynucleotide comprising the polynucleotide sequence of a SigA promoter operably linked to a polynucleotide encoding a YmaH protein wherein the chimeric polynucleotide comprises a sequence that is at least 90% identical to SEQ ID NO: 2 or SEQ ID NO:3.

2. The isolated chimeric polynucleotide of claim 1 comprising SEQ ID NO: 2 or SEQ ID NO: 3.

3. A vector comprising a polynucleotide construct comprising a polynucleotide encoding a YmaH protein, wherein said polynucleotide is operably linked to a sigA and/or a sigH promoter polynucleotide sequence, wherein said polynucleotide construct comprises a sequence that is at least 90% identical to SEQ ID NO: 2 or SEQ ID NO: 3.

4. The vector of claim 3, wherein said polynucleotide construct comprises SEQ ID NOS: 2 or SEQ ID NO: 3.

5. A modified *Bacillus* host cell comprising the vector of claim 3, wherein said modified *Bacillus* host cell has an enhanced capacity to produce a protein of interest when compared to the level of production of the same protein in a corresponding wild-type cell.

6. The modified host cell of claim 5, wherein said *Bacillus* cell is chosen from the group consisting of *B. licheniformis, B subtilis, B. lentus, B. brevis, B. stearothermophilus, B. alkalophilus, B. amyloliquefaciens, B. coagulans, B. circulans, B. lautus, B. pumilus, B. thuringiensis, B. clausii,* and *B. megaterium*.

7. The modified host cell of claim 5, wherein the protein of interest is homologous or heterologous to said modified host cell.

8. The modified host cell of claim 5, wherein the aprE promoter drives the expression of said protein of interest.

9. The modified host cell of claim 5, wherein said protein of interest is chosen from amylases, proteases, xylanases, lipases, laccases, phenol oxidases, oxidases, cutinases, cellulases, hemicellulases, esterases, peroxidases, catalases, glucose oxidases, phytases, pectinases, glucosidases, isomerases, transferases, kinases phosphatases, galactosidases and chitinases, hormones, cytokines, growth factors, receptors, vaccines, and antibodies.

10. The modified host cell of claim 5, wherein the protein of interest is an enzyme.

11. The modified host cell of claim 10, wherein said enzyme is a protease.

12. The modified host cell of claim 11, wherein said protease is a subtilisin selected from the group consisting of subtilisin 168, subtilisin BPN', subtilisin Carlsberg, *B. lentus* subtilisin, *B. clausii* subtilisin, subtilisin DY, subtilisin 147, subtilisin 309, and variants thereof.

13. The modified host cell of claim 5, wherein said cell further produces a protease, and wherein said modified cell comprises a mutation in at least one gene chosen from degU, degQ, degS, sco4, spoIIE, degQ and degR.

14. The modified host cell of claim 13, wherein said mutation is deg(Hy)32.

15. The modified host cell of claim 13, wherein said *Bacillus* cell is a *B. subtilis* cell.

16. A method for obtaining a modified *Bacillus* cell comprising:
   a) transforming a *Bacillus* host cell with the vector of claim 3, wherein said transformed *Bacillus* cell has an enhanced capacity to produce a protein of interest when compared to the level of production of the same protein in a corresponding wild-type cell; and
   b) growing said modified cell under suitable growth conditions for expressing said protein of interest.

17. The method of claim 16, wherein said vector comprising said polynucleotide construct is present on a replicating plasmid.

18. The method of claim 16, wherein said construct is integrated into the genome of said modified cell.

19. The method of claim 16, wherein said protein of interest is subtilisin.

20. A method for producing a protein of interest in a modified *Bacillus* cell capable of producing said protein of interest, said method comprising:
   a) obtaining the modified *Bacillus* cell of claim 5; and
   b) growing said modified *Bacillus* cell under suitable growth conditions for expressing said protein of interest.

21. The method of claim 20, further comprising the step of recovering said protein of interest.

22. The method of claim 20, wherein said protein of interest is produced at a time that is earlier than that at which said protein is produced in a corresponding precursor host cell.

23. The method of claim 20, wherein an aprE promoter drives the expression of said protein of interest.

24. The method of any one of claim 20, wherein said protein of interest is an enzyme.

25. A method of enhancing the expression of a protein of interest from *Bacillus* comprising:
   a) obtaining a modified *Bacillus* cell overexpressing ymaH, wherein said overexpressing comprises transforming a *Bacillus* parent host cell with a polynucleotide construct comprising a polynucleotide sequence that is at least 90% identical to a polynucleotide sequence selected from the group consisting of: SEQ ID NOS: 1, 2, 3 and 13;
   b) growing said modified *Bacillus* cell under suitable growth conditions, and
   c) allowing said protein of interest to be expressed in said modified *Bacillus* cell, wherein the expression of said protein of interest in said modified *Bacillus* cell is enhanced when compared to the expression of said protein of interest in said *Bacillus* parent host cell.

26. The method of claim 25, wherein said polynucleotide construct comprises a polynucleotide sequence chosen from SEQ ID NOS: 1, 2, 3 and 13.

27. The method of claim 25, wherein said construct is present on a plasmid or is integrated into the genome of said modified cell.

28. The method of claim 25, wherein said protein of interest is an enzyme.

* * * * *

SEQUENCE LISTING

```
<160> NUMBER OF SEQ ID NOS: 26

<210> SEQ ID NO 1
<211> LENGTH: 534
<212> TYPE: DNA
<213> ORGANISM: Artificial
<220> FEATURE:
<223> OTHER INFORMATION: constructed polynucleotide

<400> SEQUENCE: 1
ggcaccgaat tcgacgtggt ttcgcaacaa aatgcaggtc acatggttcg atatgacacc      60
gcctgttgat atggagctga aaaaaaagga aattttcaca catatagcag gaaaactcga     120
actttaatcg aaactgtatg atatagagaa tcaaggagga cgaaacatga aaccgattaa     180
tattcaggat cagtttttga atcaaatccg gaaagaaaat acgtatgtca ctgttttttt     240
gctgaacggc tttcagttgc ggggccaggt gaaaggcttt gataacttta ccgtattgtt     300
ggaatcggaa ggtaagcagc agcttatata taaacatgcg atctcaacgt ttgcgccgca     360
aaaaaacgtc cagcttgaac tcgaatagat caaaaaatgc catgtcaaga catgaggaaa     420
ggctgtcggg ggttcccggc ggccattttt aacatgaatc cacttttgct ccaagctttt     480
tgtgtaagct gaccatgcca aggcacggtc ttttttatg agggatccgg agcc            534

<210> SEQ ID NO 2
<211> LENGTH: 626
<212> TYPE: DNA
<213> ORGANISM: Artificial
<220> FEATURE:
<223> OTHER INFORMATION: constructed chimeric polynucleotide

<400> SEQUENCE: 2
gcgccgaatt ctcataccct gaaaggaaag acaaggaaa ttgtcggcaa tgagccgctc       60
ggcaggtaga aggatgttta ccgatgcaaa aaaagggcaa aatggatagg tggttgtcca    120
tgttgaatgc tataatgggg gagatttata aaagagagtg atacatattg aataatacga    180
agcagcccca cacatatagc aggaaaactc gaactttaat cgaaactgta tgatatagag    240
aatcaaggag gacgaaacat gaaaccgatt aatattcagg atcagttttt gaatcaaatc    300
cggaaagaaa atacgtatgt cactgttttt ttgctgaacg gctttcagtt gcggggccag    360
gtgaaaggct ttgataactt taccgtattg ttggaatcgg aaggtaagca gcagcttata    420
tataaacatg cgatctcaac gtttgcgccg caaaaaaacg tccagcttga actcgaatag    480
atcaaaaaat gccatgtcaa gacatgagga aaggctgtcg ggggttcccg gcggccattt    540
ttaacatgaa tccacttttg ctccaagctt tttgtgtaag ctgaccatgc caaggcacgg    600 tctttttta tgagggatcc ggtgcc                                          626
```

<210> SEQ ID NO 3
<211> LENGTH: 579
<212> TYPE: DNA
<213> ORGANISM: Artificial
<220> FEATURE:
<223> OTHER INFORMATION: constructed chimeric polynucleotide

<400> SEQUENCE: 3

```
gcgccgaatt ctcatccct gaaaggaaag acaagggaaa ttgtcggcaa tgagccgctc      60
ggcaggtaga aggatgttta ccgatgcaaa aaaagggcaa aatggatagg tggttgtcca    120
tgttgaatgc tataatgggg gagatttata aagagagtg ctcgaacttt aatcgaaact     180
gtatgatata gagaatcaag gaggacgaaa catgaaaccg attaatattc aggatcagtt    240
tttgaatcaa atccggaaag aaaatacgta tgtcactgtt tttttgctga acggctttca    300
gttgcggggc caggtgaaag ctttgataa ctttaccgta ttgttggaat cggaaggtaa     360
gcagcagctt atatataaac atgcgatctc aacgtttgcg ccgcaaaaaa acgtccagct    420
tgaactcgaa tagatcaaaa aatgccatgt caagacatga ggaaaggctg tcgggggttc    480
ccggcggcca ttttaacat gaatccactt ttgctccaag cttttttgtgt aagctgacca    540
tgccaaggca cggtcttttt ttatgaggga tccggtgcc                          579
```

<210> SEQ ID NO 4
<211> LENGTH: 73
<212> TYPE: PRT
<213> ORGANISM: Bacillus subtilis

<400> SEQUENCE: 4

```
Met Lys Pro Ile Asn Ile Gln Asp Gln Phe Leu Asn Gln Ile Arg Lys
  1               5                  10                  15
Glu Asn Thr Tyr Val Thr Val Phe Leu Leu Asn Gly Phe Gln Leu Arg
             20                  25                  30
Gly Gln Val Lys Gly Phe Asp Asn Phe Thr Val Leu Leu Glu Ser Glu
         35                  40                  45
Gly Lys Gln Gln Leu Ile Tyr Lys His Ala Ile Ser Thr Phe Ala Pro
    50                   55                  60
Gln Lys Asn Val Gln Leu Glu Leu Glu
 65                  70
```

<210> SEQ ID NO 5
<211> LENGTH: 37
<212> TYPE: DNA
<213> ORGANISM: Artificial
<220> FEATURE:
<223> OTHER INFORMATION: synthetic primer

<400> SEQUENCE: 5

```
ggcaccgaat tcgacgtggt ttcgcaacaa aatgcag                              37
```

<210> SEQ ID NO 6
<211> LENGTH: 37
<212> TYPE: DNA
<213> ORGANISM: Artificial
<220> FEATURE:
<223> OTHER INFORMATION: synthetic primer

<400> SEQUENCE: 6

```
ggcaccggat ccctcataaa aaaagaccgt gccttgg                              37
```

<210> SEQ ID NO 7
<211> LENGTH: 36
<212> TYPE: DNA

```
<213> ORGANISM: Artificial
<220> FEATURE:
<223> OTHER INFORMATION: synthetic primer

<400> SEQUENCE: 7
gcgccgaatt ctcataccct gaaaggaaag acaagg                              36

<210> SEQ ID NO 8
<211> LENGTH: 50
<212> TYPE: DNA
<213> ORGANISM: Artificial
<220> FEATURE:
<223> OTHER INFORMATION: synthetic primer

<400> SEQUENCE: 8
ttcgagtttt cctgctatat gtgtggggct gcttcgtatt attcaatatg              50

<210> SEQ ID NO 9
<211> LENGTH: 50
<212> TYPE: DNA
<213> ORGANISM: Artificial
<220> FEATURE:
<223> OTHER INFORMATION: synthetic primer

<400> SEQUENCE: 9
catattgaat aatacgaagc agccccacac atatagcagg aaaactcgaa              50

<210> SEQ ID NO 10
<211> LENGTH: 50
<212> TYPE: DNA
<213> ORGANISM: Artificial
<220> FEATURE:
<223> OTHER INFORMATION: synthetic primer

<400> SEQUENCE: 10
tgggggagat ttataaaaga gagtgctcga actttaatcg aaactgtatg              50

<210> SEQ ID NO 11
<211> LENGTH: 50
<212> TYPE: DNA
<213> ORGANISM: Artificial
<220> FEATURE:
<223> OTHER INFORMATION: synthetic primer

<400> SEQUENCE: 11
catacagttt cgattaaagt tcgagcactc tcttttataa atctcccca              50

<210> SEQ ID NO 12
<211> LENGTH: 4039
<212> TYPE: DNA
<213> ORGANISM: Artificial
<220> FEATURE:
<223> OTHER INFORMATION: synthetic plasmid sequence

<400> SEQUENCE: 12
gaattcgagc tcggtacccg ggatcctct agagtcgacc tgcaggcatg caagcttggc    60
gatcctgcct cgcgcgtttc ggtgatgacg gtgaaaacct ctgacacatg cagctcccgg  120
agacggtcac agcttgtctg taagcggatg ccgggagcag acaagcccgt cagggcgcgt  180
cagcgggtgt tggcgggtgt cggggcgcag ccatgaccca gtcacgtagc gatagcggag  240
tgtatactgg cttaactatg cggcatcaga gcagattgta ctgagagtgc accatatgcg  300
gtgtgaaata ccgcacagat gcgtaaggag aaaataccgc atcaggcgct cttccgcttc  360
ctcgctcact gactcgctgc gctcggtcgt tcggctgcgg cgagcggtat cagctcactc  420
```

```
aaaggcggta atacggttat ccacagaatc aggggataac gcaggaaaga acatgtgagc    480
aaaaggccag caaaaggcca ggaaccgtaa aaaggccgcg ttgctggcgt ttttccatag    540
gctccgcccc cctgacgagc atcacaaaaa tcgacgctca agtcagaggt ggcgaaaccc    600
gacaggacta taaagatacc aggcgtttcc ccctggaagc tccctcgtgc gctctcctgt    660
tccgaccctg ccgcttaccg gatacctgtc cgcctttctc ccttcgggaa gcgtggcgct    720
ttctcatagc tcacgctgta ggtatctcag ttcggtgtag gtcgttcgct ccaagctggg    780
ctgtgtgcac gaaccccccg ttcagcccga ccgctgcgcc ttatccggta actatcgtct    840
tgagtccaac ccgtaagac acgacttatc gccactggca gcagccactg gtaacaggat     900
tagcagagcg aggtatgtag gcggtgctac agagttcttg aagtggtggc ctaactacgg    960
ctacactaga aggacagtat ttggtatctg cgctctgctg aagccagtta ccttcggaaa   1020
aagagttggt agctcttgat ccggcaaaca aaccaccgct ggtagcggtg gtttttttgt   1080
ttgcaagcag cagattacgc gcagaaaaaa aggatctcaa gaagatcctt tgatcttttc   1140
tacggggtct gacgctcagt ggaacgaaaa ctcacgttaa gggattttgg tcatgagatt   1200
atcaaaaagg atctggagct gtaatataaa accttcttc aactaacggg gcaggttagt    1260
gacattagaa aaccgactgt aaaaagtaca gtcggcatta tctcatatta taaaagccag   1320
tcattaggcc tatctgacaa ttcctgaata gagttcataa acaatcctgc atgataacca   1380
tcacaaacag aatgatgtac ctgtaaagat agcggtaaat atattgaatt accttttatta  1440 atgaattttc ctgctgtaat aatgggtaga aggtaattac tattattatt gatatttaag   1500
ttaaacccag taaatgaagt ccatggaata atagaaagag aaaaagcatt ttcaggtata   1560
ggtgttttgg gaaacaattt ccccgaacca ttatatttct ctacatcaga aaggtataaa   1620
tcataaaact ctttgaagtc attctttaca ggagtccaaa taccagagaa tgttttagat   1680
acaccatcaa aaattgtata aagtggctct aacttatccc aataacctaa ctctccgtcg   1740
ctattgtaac cagttctaaa agctgtattt gagtttatca cccttgtcac taagaaaata   1800
aatgcagggt aaaatttata tccttcttgt tttatgtttc ggtataaaac actaatatca   1860
atttctgtgg ttatactaaa agtcgtttgt tggttcaaat aatgattaaa tatctctttt   1920
ctcttccaat tgtctaaatc aattttatta aagttcattt gatatgcctc ctaaattttt   1980
atctaaagtg aatttaggag gcttacttgt ctgctttctt cattagaatc aatccttttt   2040
taaaagtcaa tattactgta acataaatat atattttaaa aatatcccac tttatccaat   2100
tttcgtttgt tgaactaatg ggtgctttag ttgaagaata aaagaccaca ttaaaaaatg   2160
tggtcttttg tgttttttta aaggatttga gcgtagcgaa aaatcctttt ctttcttatc   2220
ttgataataa gggtaactat tgccggttgt ccattcatgg ctgaactctg cttcctctgt   2280
tgacatgaca cacatcatct caatatccga atagggccca tcagtctgac gaccaagaga   2340
gccataaaca ccaatagcct taacatcatc cccatattta ccaatattc gttccttaat   2400 ttcatgaaca atcttcattc tttcttctct agtcattatt attggtccat tcactattct   2460
cattcccttt tcagataatt ttagatttgc ttttctaaat aagaatattt ggagagcacc   2520
gttcttattc agctattaat aactcgtctt cctaagcatc cttcaatcct tttaataaca   2580
attatagcat ctaatcttca acaaactggc ccgtttgttg aactactctt taataaaata   2640 attttccgt tcccaattcc acattgcaat aatagaaaat ccatcttcat cggcttttc    2700 gtcatcatct gtatgaatca aatcgccttc ttctgtgtca tcaaggttta atttttatg    2760 tatttctttt aacaaaccac cataggagat taacctttta cggtgtaaac cttcctccaa    2820
```

-continued

| | |
|---|---|
| atcagacaaa cgtttcaaat tcttttcttc atcatcggtc ataaaatccg tatcctttac | 2880 |
| aggatatttt gcagtttcgt caattgccga ttgtatatcc gatttatatt tattttttcgg | 2940 |
| tcgaatcatt tgaactttta catttggatc atagtctaat ttcattgcct ttttccaaaa | 3000 |
| ttgaatccat tgttttttgat tcacgtagtt ttctgtattc ttaaaataag ttggttccac | 3060 |
| acataccaat acatgcatgt gctgattata agaattatct ttattattta ttgtcacttc | 3120 |
| cgttgcacgc ataaaaccaa caagattttt attaattttt ttatattgca tcattcggcg | 3180 |
| aaatccttga gccatatctg acaaactctt atttaattct tcgccatcat aaacattttt | 3240 |
| aactgttaat gtgagaaaca accaacgaac tgttggcttt tgtttaataa cttcagcaac | 3300 |
| aaccttttgt gactgaatgc catgtttcat tgctctcctc cagttgcaca ttggacaaag | 3360 |
| cctggattta caaaccaca ctcgatacaa ctttctttcg cctgtttcac gatttttgttt | 3420 |
| atactctaat atttcagcac aatctttttac tctttcagcc ttttttaaatt caagaatatg | 3480 |
| cagaagttca aagtaatcaa cattagcgat tttctttttct ctccatggtc tcacttttcc | 3540 |
| acttttttgtc ttgtccacta aaacccttga ttttttcatct gaataaatgc tactattagg | 3600 |
| acacataata ttaaaagaaa ccccccatcta tttagttatt tgtttagtca cttataactt | 3660 |
| taacagatgg ggttttttctg tgcaaccaat tttaagggtt ttcaatactt taaaacacat | 3720 |
| acataccaac acttcaacgc accttttcagc aactaaaata aaaatgacgt tatttctata | 3780 |
| tgtatcaaga taagaaagaa caagttcaaa accatcaaaa aaagacacct tttcaggtgc | 3840 |
| tttttttttatt ttataaactc attccctgat ctcgacttcg ttcttttttttt acctctcggt | 3900 |
| tatgagttag ttcaaattcg ttcttttttag gttctaaatc gtgtttttct tggaattgtg | 3960 |
| ctgttttatc ctttaccttg tctacaaacc ccttaaaaac gttttttaaag gcttttaagc | 4020 |
| cgtctgtacg ttccttaag | 4039 |

<210> SEQ ID NO 13
<211> LENGTH: 1496
<212> TYPE: DNA
<213> ORGANISM: Artificial
<220> FEATURE:
<223> OTHER INFORMATION: constructed polynucleotide

<400> SEQUENCE: 13

| | |
|---|---|
| tcatacccctg aaaggaaaga caagggaaat tgtcggcaat gagccgctcg gcaggtagaa | 60 |
| ggatgtttac cgatgcaaaa aaagggcaaa atggataggt ggttgtccat gttgaatgct | 120 |
| ataatggggg agatttataa aagagagtga tacatattga ataatacgaa gcagcccgtt | 180 |
| gtcattttag tcggaccgac ggcagtgggg aaaaccaatt taagtattca gctagccaaa | 240 |
| tccttaaacg cggaaattat cagcggagat tcgatgcaga tttataaagg gatggatatt | 300 |
| ggaacagcta aaattaccga acaggagatg gagggagtgc ccatcatct gattgacatt | 360 |
| ttagatcccc aagactcttt ctctactgcc gattatcaaa gcttagtaag aaataaaatc | 420 |
| agcgagattg caaatagagg aaagcttccg atgattgacg gcggtacagg gctttatata | 480 |
| caatctgagc tttacgatta tacatttacg gaagaggcaa atgatcccgt gtttcgagag | 540 |
| agcatgcaaa tggctgctga gcgggaaggc gctgactttc ttcatgccaa acttgctgca | 600 |
| gcagatcccg aggcagcagc tgcgattcat ccgaataata caagaagagt cattcgcgca | 660 |
| ctggaaattt tacatacgtc cggaaaaacg atgtcccagc atttgaagga acaaaaacga | 720 |
| gaacttctgt acaatgcagt gttaattggc ctgacaatgg atagagacac gctttacgaa | 780 |
| agaattaatc agcgggtcga tttgatgatg cagtcaggcc ttcttccgga agtgaaacgc | 840 |

```
ttatacgaca agaacgtgag agactgtcaa tcaatacagg cgataggcta taaagagctg    900
tatgcatatt ttgacggttt tgtgacactt tccgatgctg tcgaacagct aaagcagaac    960
tcgaggcggt atgcgaaacg ccagctgacg tggtttcgca acaaaatgca ggtcacatgg   1020
ttcgatatga caccgcctgt tgatatggag ctgaaaaaaa aggaaatttt cacacatata   1080
gcaggaaaac tcgaacttta atcgaaactg tatgatatag agaatcaagg aggacgaaac   1140
atgaaaccga ttaatattca ggatcagttt ttgaatcaaa tccggaaaga aaatacgtat   1200
gtcactgttt ttttgctgaa cggctttcag ttgcggggcc aggtgaaagg ctttgataac   1260
tttaccgtat tgttggaatc ggaaggtaag cagcagctta tatataaaca tgcgatctca   1320
acgtttgcgc cgcaaaaaaa cgtccagctt gaactcgaat agatcaaaaa atgccatgtc   1380
aagacatgag gaaaggctgt cggggggttcc cggcggccat ttttaacatg aatccacttt   1440
tgctccaagc ttttttgtgta agctgaccat gccaaggcac ggtctttttt tatgag        1496

<210> SEQ ID NO 14
<211> LENGTH: 156
<212> TYPE: DNA
<213> ORGANISM: Bacillus subtilis

<400> SEQUENCE: 14 tcatacccctg aaaggaaaga caagggaaat tgtcggcaat gagccgctcg gcaggtagaa     60
ggatgtttac cgatgcaaaa aaagggcaaa atggataggt ggttgtccat gttgaatgct    120
ataatggggg agatttataa aagagagtga tacata                              156

<210> SEQ ID NO 15
<211> LENGTH: 945
<212> TYPE: DNA
<213> ORGANISM: Bacillus subtilis

<400> SEQUENCE: 15
ttgaataata cgaagcagcc cgttgtcatt ttagtcggac cgacggcagt ggggaaaacc     60
aatttaagta ttcagctagc caaatcctta aacgcggaaa ttatcagcgg agattcgatg    120
cagatttata aagggatgga tattggaaca gctaaaatta ccgaacagga gatggaggga    180
gtgccccatc atctgattga cattttagat ccccaagact cttttctctac tgccgattat    240 caaagcttag taagaaataa aatcagcgag attgcaaata gaggaaagct tccgatgatt    300
gacggcggta cagggcttta tatacaatct gagctttacg attatacatt tacggaagag    360
gcaaatgatc ccgtgtttcg agagagcatg caaatggctg ctgagcggga aggcgctgac    420
tttcttcatg ccaaacttgc tgcagcagat cccgaggcag cagctgcgat tcatccgaat    480
aatacaagaa gagtcattcg cgcactgaa attttacata cgtccggaaa aacgatgtcc    540
cagcatttga aggaacaaaa acgagaactt ctgtacaatg cagtgttaat tggcctgaca    600
atggatagag acacgcttta cgaaagaatt aatcagcggg tcgatttgat gatgcagtca    660
ggccttcttc cggaagtgaa acgcttatac gacaagaacg tgagagactg tcaatcaata    720
caggcgatag gctataaaga gctgtatgca tattttgacg gttttgtgac actttccgat    780
gctgtcgaac agctaaagca gaactcgagg cggtatgcga aacgccagct gacgtggttt    840
cgcaacaaaa tgcaggtcac atggttcgat atgacaccgc ctgttgatat ggagctgaaa    900
aaaaaggaaa ttttcacaca tatagcagga aaactcgaac tttaa                    945

<210> SEQ ID NO 16
<211> LENGTH: 82
<212> TYPE: DNA
```

```
<213> ORGANISM: Bacillus subtilis

<400> SEQUENCE: 16
aaaggaaatt ttcacacata tagcaggaaa actcgaactt taatcgaaac tgtatgatat    60
agagaatcaa ggaggacgaa ac                                             82

<210> SEQ ID NO 17
<211> LENGTH: 222
<212> TYPE: DNA
<213> ORGANISM: Bacillus subtilis

<400> SEQUENCE: 17
atgaaaccga ttaatattca ggatcagttt ttgaatcaaa tccggaaaga aaatacgtat    60
gtcactgttt ttttgctgaa cggctttcag ttgcggggcc aggtgaaagg ctttgataac   120
tttaccgtat tgttggaatc ggaaggtaag cagcagctta tatataaaca tgcgatctca   180
acgtttgcgc cgcaaaaaaa cgtccagctt gaactcgaat ag                      222

<210> SEQ ID NO 18
<211> LENGTH: 42
<212> TYPE: DNA
<213> ORGANISM: Artificial
<220> FEATURE:
<223> OTHER INFORMATION: synthetic primer

<400> SEQUENCE: 18
gcgcgcgaat tcagggaaat tgtcggcaat gagccgctcg gc                       42

<210> SEQ ID NO 19
<211> LENGTH: 41
<212> TYPE: DNA
<213> ORGANISM: Artificial
<220> FEATURE:
<223> OTHER INFORMATION: synthetic primer

<400> SEQUENCE: 19
gcgcgccatg gctgattcgt ctcagttctg cttcactttc a                        41

<210> SEQ ID NO 20
<211> LENGTH: 4768
<212> TYPE: DNA
<213> ORGANISM: Artificial
<220> FEATURE:
<223> OTHER INFORMATION: synthetic pBN3 vector sequence

<400> SEQUENCE: 20
gacgtctaag aaaccattat tatcatgaca ttaacctata aaaataggcg tatcacgagg    60
ccctttcgtc ttcaagaatt aattctcatg tttgacagct tatcatcgat aagcttgcat   120
gcctgcaggt cgactctaga ggatccccgg gtaccgagct cgaattcctt aaggaacgta   180
cagacggctt aaaagccttt aaaaacgttt taagggggtt tgtagacaag gtaaggata    240 aaacagcaca attccaagaa aaacacgatt tagaacctaa aaagaacgaa tttgaactaa   300
ctcataaccg agaggtaaaa aaagaacgaa gtcgagatca gggaatgagt ttataaaata   360
aaaaaagcac ctgaaaaggt gtctttttt  gatggttttg aacttgttct ttcttatctt   420
gatacatata gaaataacgt catttttatt ttagttgctg aaaggtgcgt tgaagtgttg   480
gtatgtatgt gttttaaagt attgaaaacc cttaaaattg gttgcacaga aaacccccat   540
ctgttaaagt tataagtgac taaacaaata actaaataga tggggggtttc ttttaatatt   600 atgtgtccta atagtagcat ttattcgat gaaaaatcaa gggttttagt ggacaagaca   660
```

```
aaaagtggaa aagtgagacc atggagagaa aagaaaatcg ctaatgttga ttactttgaa      720
cttctgcata ttcttgaatt taaaaaggct gaaagagtaa aagattgtgc tgaaatatta      780
gagtataaac aaaatcgtga aacaggcgaa agaaagttgt atcgagtgtg gttttgtaaa      840
tccaggcttt gtccaatgtg caactggagg agagcaatga aacatggcat tcagtcacaa      900
aaggttgttg ctgaagttat taaacaaaag ccaacagttc gttggttgtt tctcacatta      960
acagttaaaa atgtttatga tggcgaagaa ttaaataaga gtttgtcaga tatggctcaa     1020
ggatttcgcc gaatgatgca atataaaaaa attaataaaa atcttgttgg ttttatgcgt     1080
gcaacggaag tgacaataaa taataaagat aattcttata atcagcacat gcatgtattg     1140
gtatgtgtgg aaccaactta ttttaagaat acagaaaact acgtgaatca aaacaatgg      1200 attcaatttt ggaaaaaggc aatgaaatta gactatgatc caaatgtaaa agttcaaatg     1260
attcgaccga aaaataaata taaatcggat atacaatcgg caattgacga aactgcaaaa     1320
tatcctgtaa aggatacgga ttttatgacc gatgatgaag aaaagaattt gaaacgtttg     1380
tctgatttgg aggaaggttt acaccgtaaa aggttaatct cctatggtgg tttgttaaaa     1440
gaaatacata aaaaattaaa ccttgatgac acagaagaag gcgatttgat tcatacagat     1500
gatgacgaaa agccgatga agatggattt tctattattg caatgtggaa ttgggaacgg      1560
aaaaattatt ttattaaaga gtagttcaac aaacgggcca gtttgttgaa gattagatgc     1620
tataattgtt attaaaagga ttgaaggatg cttaggaaga cgagttatta atagctgaat     1680
aagaacggtg ctctccaaat attcttattt agaaaagcaa atctaaaatt atctgaaaag     1740
ggaatgagaa tagtgaatgg accaataata atgactagag aagaaagaat gaagattgtt     1800
catgaaatta aggaacgaat attggataaa tatggggatg atgttaaggc tattggtgtt     1860
tatggctctc ttggtcgtca gactgatggg ccctattcgg atattgagat gatgtgtgtc     1920
atgtcaacag aggaagcaga gttcagccat gaatggacaa ccggtgagtg gaaggtggaa     1980
gtgaattttg atagcgaaga gattctacta gattatgcat ctcaggtgga atcagattgg     2040
ccgcttacac atggtcaatt tttctctatt ttgccgattt atgattcagg tggatactta     2100
gagaaagtgt atcaaactgc taaatcggta gaagcccaaa cgttccacga tgcgatttgt     2160
gcccttatcg tagaagagct gtttgaatat gcaggcaaat ggcgtaatat tcgtgtgcaa     2220
ggaccgacaa catttctacc atccttgact gtacaggtag caatggcagg tgccatgttg     2280
attggtctgc atcatcgcat ctgttatacg acgagcgctt cggtcttaac tgaagcagtt     2340
aagcaatcag atcttccttc aggttatgac catctgtgcc agttcgtaat gtctggtcaa     2400 cttttccgact ctgagaaact tctggaatcg ctagagaatt tctggaatgg gattcaggag     2460
tggacagaac gacacggata tatagtggat gtgtcaaaac gcataccatt ttgaacgatg     2520
acctctaata attgttaatc atgttggtta cctgcctcgc gcgtttcggt gatgacggtg     2580
aaaacctctg acacatgcag ctcccggaga cggtcacagc ttgtctgtaa gcggatgccg     2640
ggagcagaca agcccgtcag ggcgcgtcag cgggtgttgg cgggtgtcgg ggcgcagcca     2700
tgacccagtc acgtagcgat agcggagtgt atactggctt aactatgcgg catcagagca     2760
gattgtactg agagtgcacc atatgcggtg tgaaataccg cacagatgcg taaggagaaa     2820
ataccgcatc aggcgctctt ccgcttcctc gctcactgac tcgctgcgct cggtcgttcg     2880
gctgcggcga gcggtatcag ctcactcaaa ggcggtaata cggttatcca cagaatcagg     2940
ggataacgca ggaaagaaca tgtgagcaaa aggccagcaa aaggccagga accgtaaaaa     3000
ggccgcgttg ctggcgtttt tccataggct ccgcccccct gacgagcatc acaaaaatcg     3060
```

```
acgctcaagt cagaggtggc gaaacccgac aggactataa agataccagg cgttccccc     3120 tggaagctcc ctcgtgcgct ctcctgttcc gaccctgccg cttaccggat acctgtccgc   3180
ctttctccct tcgggaagcg tggcgctttc tcatagctca cgctgtaggt atctcagttc   3240
ggtgtaggtc gttcgctcca agctgggctg tgtgcacgaa ccccccgttc agcccgaccg   3300
ctgcgcctta tccggtaact atcgtcttga gtccaacccg gtaagacacg acttatcgcc   3360
actggcagca gccactggta acaggattag cagagcgagg tatgtaggcg gtgctacaga   3420
gttcttgaag tggtggccta actacggcta cactagaagg acagtatttg gtatctgcgc   3480
tctgctgaag ccagttacct tcggaaaaag agttggtagc tcttgatccg gcaaacaaac   3540
caccgctggt agcggtggtt ttttgtttg caagcagcag attacgcgca gaaaaaaggg   3600
atctcaagaa gatcctttga tcttttctac ggggtctgac gctcagtgga acgaaaactc   3660
acgttaaggg attttggtca tgagattatc aaaaaggatc ttcacctaga tccttttaaa   3720
ttaaaaatga agttttaaat caatctaaag tatatatgag taaacttggt ctgacagtta   3780
ccaatgctta atcagtgagg cacctatctc agcgatctgt ctatttcgtt catccatagt   3840
tgcctgactc cccgtcgtgt agataactac gatacgggag ggcttaccat ctggccccag   3900
tgctgcaatg ataccgcgag acccacgctc accggctcca gatttatcag caataaacca   3960
gccagccgga agggccgagc gcagaagtgg tcctgcaact ttatccgcct ccatccagtc   4020
tattaattgt tgccgggaag ctagagtaag tagttcgcca gttaatagtt tgcgcaacgt   4080
tgttgccatt gctacaggca tcgtggtgtc acgctcgtcg tttggtatgg cttcattcag   4140
ctccggttcc caacgatcaa ggcgagttac atgatccccc atgttgtgca aaaaagcggt   4200
tagctccttc ggtcctccga tcgttgtcag aagtaagttg gccgcagtgt tatcactcat   4260
ggttatggca gcactgcata attctcttac tgtcatgcca tccgtaagat gcttttctgt   4320
gactggtgag tactcaacca agtcattctg agaatagtgt atgcggcgac cgagttgctc   4380
ttgcccggcg tcaatacggg ataataccgc gccacatagc agaactttaa aagtgctcat   4440
cattggaaaa cgttcttcgg ggcgaaaact ctcaaggatc ttaccgctgt tgagatccag   4500
ttcgatgtaa cccactcgtg cacccaactg atcttcagca tcttttactt tcaccagcgt   4560
ttctgggtga gcaaaaacag gaaggcaaaa tgccgcaaaa aagggaataa gggcgacacg   4620
gaaatgttga atactcatac tcttcctttt tcaatattat tgaagcattt atcagggtta   4680
ttgtctcatg agcggataca tatttgaatg tatttagaaa aataaacaaa tagggggttcc   4740 gcgcacattt ccccgaaaag tgccacct                                      4768
```

<210> SEQ ID NO 21
<211> LENGTH: 7
<212> TYPE: DNA
<213> ORGANISM: Bacillus subtilis

<400> SEQUENCE: 21 aagagag                                                              7

<210> SEQ ID NO 22
<211> LENGTH: 5
<212> TYPE: DNA
<213> ORGANISM: Bacillus subtilis

<400> SEQUENCE: 22 ggagg                                                                5

<210> SEQ ID NO 23

```
<211> LENGTH: 46
<212> TYPE: DNA
<213> ORGANISM: Artificial
<220> FEATURE:
<223> OTHER INFORMATION: consensus sigmaA promoter sequence

<400> SEQUENCE: 23
tgggtcttga caaatattat tccatctatt acaataaatt cacaga            46

<210> SEQ ID NO 24
<211> LENGTH: 46
<212> TYPE: DNA
<213> ORGANISM: Bacillus sp.

<400> SEQUENCE: 24
tgggtctact aaaatattat tccatctatt acaataaatt cacaga            46

<210> SEQ ID NO 25
<211> LENGTH: 46
<212> TYPE: DNA
<213> ORGANISM: Artificial
<220> FEATURE:
<223> OTHER INFORMATION: synthetic mutant aprE promoter

<400> SEQUENCE: 25
tgggtcttga caaatattat tccatctatt acaataaatt cacaga            46

<210> SEQ ID NO 26
<211> LENGTH: 4
<212> TYPE: PRT
<213> ORGANISM: Artificial
<220> FEATURE:
<223> OTHER INFORMATION: synthetic substrate

<400> SEQUENCE: 26

Ala Ala Pro Phe
1
```